US007388032B2

(12) United States Patent
Saikawa et al.

(10) Patent No.: US 7,388,032 B2
(45) Date of Patent: Jun. 17, 2008

(54) SUSTAINED RELEASE COMPOSITIONS, PROCESS FOR PRODUCING THE SAME AND UTILIZATION THEREOF

(75) Inventors: Akira Saikawa, Nagaokakyo (JP); Yasutaka Igari, Kobe (JP); Yoshio Hata, Toyonaka (JP); Kazumichi Yamamoto, Nara (JP)

(73) Assignee: Takeda Pharmaceutical Company Limited, Osaka (JP)

(*) Notice: Subject to any disclaimer, the term of this patent is extended or adjusted under 35 U.S.C. 154(b) by 793 days.

(21) Appl. No.: 10/799,320

(22) Filed: Mar. 12, 2004

(65) Prior Publication Data

US 2005/0025826 A1 Feb. 3, 2005

Related U.S. Application Data

(62) Division of application No. 09/582,926, filed as application No. PCT/JP99/00086 on Jan. 13, 1999, now Pat. No. 6,740,634.

(30) Foreign Application Priority Data

Jan. 16, 1998 (JP) .................................. 10-06412

(51) Int. Cl.
*A61K 47/00* (2006.01)
(52) U.S. Cl. .............................. 514/772.1; 514/772.6; 514/2
(58) Field of Classification Search ................ 424/468, 424/426; 514/2, 468
See application file for complete search history.

(56) References Cited

U.S. PATENT DOCUMENTS

| 4,049,640 | A | | 9/1977 | Conrow et al. |
|---|---|---|---|---|
| 4,272,398 | A | * | 6/1981 | Jaffe ..................... 427/213.31 |
| 5,270,305 | A | | 12/1993 | Palmer |
| 5,705,194 | A | | 1/1998 | Wong et al. |
| 5,821,623 | A | | 10/1998 | Larson |
| 5,840,835 | A | * | 11/1998 | Adams et al. .............. 530/323 |
| 5,869,097 | A | | 2/1999 | Wong et al. |
| 6,132,768 | A | | 10/2000 | Sachs et al. |
| 7,265,157 | B1 | | 9/2007 | Igari et al. |
| 2003/0134800 | A1 | | 7/2003 | Yamamoto et al. |

FOREIGN PATENT DOCUMENTS

| WO | WO 96/22786 | 8/1996 |
|---|---|---|
| WO | WO 97/35563 | 10/1997 |
| WO | WO 98/20836 | 5/1998 |
| WO | WO 98/32423 | 7/1998 |
| WO | WO 01/05380 A1 | 1/2001 |
| WO | WO 03/002092 | 1/2003 |

OTHER PUBLICATIONS

A.M Al-Naggar, F.S.M. Ahmed, M.F. Badie and K.M. Kamel, Synthesis of some 3-hydroxynaphthalene-2-carbonylamino acid dipeptide derivatives, Int. J. Protein Peptide Res. (1983) 22:251-6.*
U.S. Appl. No. 11/782,707, filed Jul. 25, 2007, Igari et al.

* cited by examiner

*Primary Examiner*—Michael P. Woodward
*Assistant Examiner*—Jeffrey Eberhard
(74) *Attorney, Agent, or Firm*—Foley & Lardner LLP

(57) ABSTRACT

A sustained-release composition containing a hydroxynaphthoic acid salt of a biologically active substance and a biodegradable polymer, a method of its production, and a pharmaceutical composition containing said sustained-release composition.

9 Claims, No Drawings

SUSTAINED RELEASE COMPOSITIONS, PROCESS FOR PRODUCING THE SAME AND UTILIZATION THEREOF

This application is a divisional of U.S. patent application Ser. No. 09/582,926, filed Jun. 5, 2000, now U.S. Pat. No. 6,740,634, issued May 25, 2004, which was the National Phase filing of International Patent Application No. PCT/JP99/00086, filed Jan. 13, 1999.

FIELD OF INDUSTRIAL APPLICATION

The present invention relates to a sustained-release composition of a biologically active substance, and a production method thereof.

PRIOR ART

Japanese Patent Unexamined Publication No. 97334/1995 discloses a sustained-release preparation comprising a biologically active peptide or salt thereof and a biodegradable polymer having a free carboxyl group at one end, and a production method thereof.

The patent publications for GB2209937, GB2234169, GB2234896, GB2257909 and EP626170A2 disclose compositions based on a biodegradable polymer containing a separately prepared water-insoluble salt, such as a pamoate of a peptide or protein, or production methods therefore.

The patent publication for WO95/15767 discloses the embonate (pamoate) of cetrorelix (LH-RH antagonist) and a production method therefore, and describes that the peptide-releasing profile of this pamoate remains the same as in its use alone, even when included in a biodegradable polymer.

Problems to be Solved by the Invention

To provide a novel composition that contains a high concentration of biologically active substance, and that is capable of a controlled rate of release.

Means of Solving the Problems

After extensive investigation aiming at resolving the above problem, the present inventors found that when the a biologically active substance is incorporated in high concentration in a composition by allowing the biologically active substance and the hydroxynaphthoic acid to be co-present during formation of the composition, and when both are included in a biodegradable polymer, the biologically active substance is release at rates differing from those of the biologically active substance from the counterpart composition of the biologically active substance and hydroxynaphthoic acid prepared in the absence of the biodegradable polymer, which rate of release is controllable by choosing the appropriate kind of biodegradable polymer. The inventors conducted further investigations based on this finding, and developed the present invention.

Accordingly, the present invention provides:

(1) a sustained-release composition containing a biologically active substance or salt thereof, a hydroxynaphthoic acid or salt thereof, and a biodegradable polymer or salt thereof, (2) a sustained-release composition according to term (1) above wherein the biologically active substance is a biologically active peptide, (3) a sustained-release composition according to term (2) above wherein the biologically active peptide is an LH-RH derivative, (4) a sustained-release composition according to term (1) above wherein the hydroxynaphthoic acid is 3-hydroxy-2-naphthoic acid, (5) a sustained-release composition according to term (1) above wherein the biodegradable polymer is an alpha.-hydroxycarboxylic acid polymer, (6) a sustained-release composition according to term (5) above wherein the a-hydroxycarboxylic acid polymer is a lactic acid-glycolic acid polymer, (7) a sustained-release composition according to term (6) above wherein the content ratio of lactic acid and glycolic acid is 100/0 to 40/60 mol %, (8) a sustained-release composition according to term (7) above wherein the content ratio of lactic acid and glycolic acid is 100/0 mol %, (9) a sustained-release composition according to term (6) above wherein the weight-average molecular weight of the polymer is about 3,000 to about 100,000,

(10) a sustained-release composition according to term (9) above wherein the weight-average molecular weight of the polymer is about 20,000 to about 50,000,

(11) a sustained-release composition according to term (3) above, wherein the LH-RH derivative is a peptide represented by the formula:

5-oxo-Pro-His-Trp-Ser-Tyr-Y-Leu-Arg-Pro-Z     (SEQ ID NO.:1)

wherein Y represents DLeu, DAla, DTrp, DSer(tBu), D2Nal or DHis(ImBzl); Z represents NH—$C_2H_5$ or Gly-$NH_2$,

(12) a sustained-release composition according to term (6) above, wherein the terminal carboxyl group content of the polymer is 50-90 micromol per unit mass (gram) of the polymer,

(13) a sustained-release composition according to term (3) above, wherein the molar ratio of the hydroxynaphthoic acid or salt thereof and the LH-RH derivative or salt thereof is from 3 to 4 to 4 to 3,

(14) a sustained-release composition according to term (13) above, wherein the LH-RH derivative or salt thereof is contained at 14% (w/w) to 24% (w/w),

(15) a sustained-release composition according to term (1) above, wherein the bioactive substance or salt thereof is very slightly soluble in water or soluble in water,

(16) a sustained-release composition according to term (1) above, which is intended for injection,

(17) a method of producing the sustained-release composition according to term (1) above, comprising removing the solvent from a mixture of a bioactive substance or salt thereof, a biodegradable polymer or salt thereof, and hydroxynaphthoic acid or a salt thereof,

(18) a method of producing the sustained-release composition according to term (17) above, comprising mixing and dispersing a bioactive substance or salt thereof in an organic solvent solution containing a biodegradable polymer or salt thereof and hydroxynaphthoic acid or a salt thereof, and subsequently removing the organic solvent,

(19) a method of producing the sustained-release composition according to term (18) above, wherein the bioactive substance or salt thereof is in the form of an aqueous solution,

(20) a production method according to term (17) above, wherein the salt of the bioactive substance is a salt with a free base or acid,

(21) a pharmaceutical containing the sustained-release composition according to term (1) above,
(22) an agent for preventing or treating prostatic cancer, prostatic hypertrophy, endometriosis, hysteromyoma, metrofibroma, precocious puberty, dysmenorrheal, or breast cancer, or a contraceptive, containing the sustained-release composition according to term (3) above,
(23) a sustained-release composition containing the hydroxynaphthoate of a bioactive substance and a biodegradable polymer or salt thereof,
(24) a method of suppressing bioactive substance initial burst from a sustained-release composition, comprising using hydroxynaphthoic acid or a salt thereof,
(25) a method of increasing the efficiency of bioactive substance inclusion in a sustained-release composition, comprising using hydroxynaphthoic acid or a salt thereof,
(26) a hydroxynaphthoate of a bioactive peptide,
(27) a hydroxynaphthoate of a bioactive peptide according to term (26) above, which is soluble in water or very slightly soluble in water, and
(28) a sustained-release composition containing the hydroxynaphthoate of a bioactive peptide.
The present invention further provides:
(29) a sustained-release composition according to term (28) above, wherein the content of the hydroxynaphthoic acid or salt thereof is about 1 to about 7 mol, preferably about 1 to about 2 mol, per mol of the bioactive peptide or salt thereof
(30) a production method for the sustained-release composition according to term (17) above, comprising producing a W/O emulsion with a solution containing a bioactive substance or salt thereof as an internal aqueous phase and a solution containing a biodegradable polymer and hydroxynaphthoic acid or a salt thereof as an oil phase, and subsequently removing the solvent,
(31) a production method for the sustained-release composition according to term (17) above, comprising producing a W/O emulsion with a solution containing hydroxynaphthoic acid or a salt thereof as an internal aqueous phase and a solution containing a bioactive substance or salt thereof and a biodegradable polymer or salt thereof as an oil phase, and subsequently removing the solvent,
(32) a production method for the sustained-release composition according to term (28) above, comprising mixing and dissolving a bioactive peptide or salt thereof and hydroxynaphthoic acid or salt thereof, and subsequently removing the solvent, and
(33) the production method for sustained-release composition according to any one of terms (30) through (32), wherein the solvent removal method is water-in drying method.

The biologically active substance used in the present invention is not subject to limitation, as long as it is pharmacologically useful, and it may be a non-peptide substance or a peptide substance. The non-peptide substance includes an agonist, an antagonist, and a substance having an enzyme inhibitory activity. The peptide substance includes, for example, biologically active peptides, and particularly those having molecular weights of about 300 to about 40,000, preferably about 400 to about 30,000, and more preferably about 500 to about 20,000.

Such biologically active peptides include, for example, luteinizing hormone-releasing hormone (LH-RH), insulin, somatostatin, growth hormones, growth hormone-releasing hormone (GH-RH), prolactin, erythropoietin, adrenocorticotropic hormone, melanocyte-stimulating hormone, thyroid hormone-releasing hormone, thyroid-stimulating hormone, luteinizing hormone, follicle-stimulating hormone, vasopressin, oxytocin, calcitonin, gastrin, secretin, pancreozymin, cholecystokinin, angiotensin, human placental lactogen, human chorionic gonadotropin, enkephalin, endorphin, kyotorphin, tuftsin, thymopoietin, thymosin, thymostimulin, thymic humoral factor, blood thymic factor, tumor necrosis factor, colony-stimulating factor, motilin, daynorphin, bombesin, neurotensin, caerulein, bradykinin, atrial natriuresis-increasing factor, nerve growth factor, cell growth factor, neurotrophic factor, endothelin-antagonistic peptides, derivatives thereof, fragments of these peptides, and derivatives of such fragments.

The biologically active peptide used in the present invention may be as is, or may be a pharmacologically acceptable salt.

Such salts include salts with inorganic acids (which may also be referred to as inorganic free acids) (e.g., carbonic acid, bicarbonic acid, hydrochloric acid, sulfuric acid, nitric acid, boric acid), organic acids (which may also be referred to as organic free acids) (e.g., succinic acid, acetic acid, propionic acid, trifluoroacetic acid) etc., when said biologically active peptide has a basic group such as an amino group.

When said biologically active peptide has an acidic group such as a carboxyl group, such salts include salts with inorganic bases (which may also be referred to as inorganic free bases) (e.g., alkali metals such as sodium and potassium, alkaline earth metals such as calcium and magnesium), organic bases (which may also be referred to as organic free bases) (e.g., organic amines such as triethylamine, basic amino acids such as arginine) etc. The biologically active peptide may form a metal complex compound (e.g., copper complex, zinc complex).

Preferred examples of the above-described biologically active peptide are LH-RH derivatives or salts thereof that are effective against sex hormone-dependent diseases such as prostatic cancer, prostatic hypertrophy, endometriosis, hysteromyoma, precocious puberty and breast cancer, and effective for contraception.

Examples of LH-RH derivatives or salts thereof include, for example, the peptides described in "Treatment with GnRH Analogs: Controversies and Perspectives" (The Parthenon Publishing Group Ltd., published 1996), Japanese Patent Examined Publication No. 503165/1991, Japanese Patent Unexamined Publication Nos. 101695/1991, 97334/1995 and 259460/1996, and elsewhere.

LH-RH derivatives may be LH-RH agonists or LH-RH antagonists; useful LH-RH antagonists include, for example, biologically active peptides represented by general formula [I]:

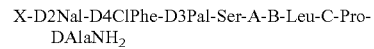
    DAlaNH$_2$    (SEQ ID NO.: 2)

[X represents N(4H$_2$-furoyl)Gly or NAc; A represents a residue selected from NMeTyr, Tyr, Aph(Atz) and NMeAph (Atz); B represents a residue selected from DLys(Nic), DCit, DLys(AzaglyNic), DLys(AzaglyFur), DhArg(Et$_2$), DAph (Atz) and DhCi; C represents Lys(Nisp), Arg or hArg(Et$_2$)] or salts thereof.

Useful LH-RH agonists include, for example, biologically active peptides represented by general formula [II]:

[Y represents a residue selected from DLeu, DAla, DTrp, DSer(tBu), D2Nal and DHis(1mBzl); Z represents $NH_2$—$C_2$—$H_5$, Gly-$NH_2$] or salts thereof. Peptides wherein Y is DLeu and Z is NH—$C_2$—$H_5$, (i.e., a peptide represented by the formula: 5-oxo-Pro-His-Trp-Ser-Tyr-DLeu-Arg-Pro-NH—$C_2H_5$ (SEQ ID NO.:3) in particular, are preferred.

These peptides can be produced by the methods described in the above-mentioned references or patent publications, or methods based thereon.

The abbreviations used herein are defined as follows:
Abbreviation Name
N(4H$_2$-furoyl)Gly: N-tetrahydrofuroylglycine residue
NAc: N-acetyl group
D2Nal: D-3-(2-naphthyl)alanine residue
D4ClPhe: D-3-(4-chloro)phenylalanine residue
D3Pal: D-3-(3-pyridyl)alanine residue
NMeTyr: N-methyltyrosine residue
Aph(Atz): N-[5'-(3'-amino-1'H-1',2',4'-triazolyl)]phenylalanine residue
NMeAph(Atz): N-methyl-[5'-(3'-amino-1'H-1',2',4'-triazolyl)]phenylalanine residue
DLys(Nic): D-(e-N-nicotinoyl)lysine residue
Dcit: D-citrulline residue
DLys(AzaglyNic): D-(azaglycylnicotinoyl)lysine residue
DLys(AzaglyFur): D-(azaglycylfuranyl)lysine residue
DhArg(Et$_2$): D-(N,N'-diethyl)homoarginine residue
DAph(Atz): D-N-[5'-(3'-amino-1'H-1',2',4'-triazolyl)]phenylalanine residue
DhCi: D-homocitrulline residue
Lys(Nisp): (e-N-isopropyl)lysine residue
hArg(Et$_2$): (N,N'-diethyl)homoarginine residue The abbreviations for amino acids are based on abbreviations specified by the IUPAC-IUB Commission on Biochemical Nomenclature [European Journal of Biochemistry, Vol. 138, pp. 9-37 (1984)] or abbreviations in common use in relevant fields. When an optical isomer may be present in amino acid, it is of the L-configuration, unless otherwise stated.

The hydroxynaphthoic acid for the present invention consists of a naphthalene ring and 1 hydroxyl group and 1 carboxyl group, both groups binding to different carbons of the ring. There are therefore a total of 14 isomers with the hydroxyl group located at different positions with respect to the carboxyl group located at positions 1 and 2 of the naphthalene ring. Any of these isomers can be used, and their mixtures in any ratios can be used. As described later, it is preferable that the acid dissociation constant be great, or pKa (pKa=$-\log_{10}$Ka, Ka represents acid dissociation constant) be small. Preference is also given to isomers that are very slightly soluble in water.

Isomers that are soluble in alcohols (e.g., ethanol, methanol) are preferred. The term "soluble in alcohols," as used herein, means that the solubility is not less than 10 g/l in methanol, for example.

Regarding the pKa values of the above-described hydroxynaphthoic acid isomers, the only known value is for 3-hydroxy-2-naphthoic acid (pKa=2.708, Kagaku Binran Kisohen II, Chemical Society of Japan, published Sep. 25, 1969; however, useful information is obtained by comparing the pKa values of three isomers of hydroxybenzoic acid. Specifically, the pKa values of m-hydroxybenzoic acid and p-hydroxybenzoic acid are not less than 4, whereas the pKa value of o-hydroxybenzoic acid (salicylic acid) (=2.754) is extremely small. Of the above-mentioned 14 isomers, those consisting of a naphthalene ring and a carboxyl group and a hydroxyl group, both bound to adjoining carbon atoms of the ring, i.e., 3-hydroxy-2-naphthoic acid, 1-hydroxy-2-naphthoic acid, and 2-hydroxy-1-naphthoic acid are therefore preferred. Furthermore, 3-hydroxy-2-naphthoic acid, which consists of a naphthalene ring and a hydroxyl group bound to the carbon at position 3 of the ring and 1 carboxyl group bound to the carbon at position 2 of the ring, is preferred.

The hydroxynaphthoic acid may be a salt. Salts include, for example, salts with inorganic bases (e.g., alkali metals such as sodium and potassium, alkaline earth metals such as calcium and magnesium), organic bases (e.g., organic amines such as triethylamine, basic amino acids such as arginine), and salts and complex salts with transition metals (e.g., zinc, iron, copper).

An example method of preparing the hydroxynaphthoic acid salt of the bioactive substance of the present invention is given below.

(1) A hydrated organic solvent solution of hydroxynaphthoic acid is passed through a weakly basic ion exchange column to adsorb the acid and saturate the column. The excess portion of the hydroxynaphthoic acid is then removed through the hydrated organic solvent, after which a hydrated organic solvent solution of the bioactive substance or salt thereof is passed through the column to cause ion exchange; the solvent is removed from the effluent obtained. Useful organic solvents in said hydrated organic solvent include alcohols (e.g., methanol, ethanol), acetonitrile, tetrahydrofuran, and dimethylformamide. Solvent removal for salt precipitation is achieved using a commonly known method or a method based thereon. Examples of such methods include the method in which the solvent is evaporated, with the degree of vacuum adjusted using a rotary evaporator etc.

(2) Through a weakly basic ion exchange column, previously subjected to ion exchange to hydroxide ions, a hydrated organic solvent solution of the bioactive substance or salt thereof is passed, to convert the basic groups to the hydroxide type. Hydroxynaphthoic acid in an amount not more than the molar equivalent is added to the effluent recovered, and dissolved, followed by concentration; the salt precipitated is washed with water as necessary, and dried.

Because the hydroxynaphthoic acid salt of a bioactive substance is very slightly soluble in water, although also depending on the bioactive substance used, said salt itself of a bioactive peptide, exhibiting potential for sustained-release, can be used for a sustained-release preparation of a bioactive substance, and can also be used to produce a sustained-release composition.

Biodegradable polymers used in the present invention include, for example, polymers and copolymers that have been synthesized from one or more kinds selected from α-hydroxymonocarboxylic acids (e.g., glycolic acid, lactic acid), hydroxydicarboxylic acids (e.g., malic acid), hydroxytricarboxylic acids (e.g., citric acid) etc., and that have a free carboxyl group, or mixtures thereof; poly-α-cyanoacrylic acid esters; polyamino acids (e.g., poly-g-benzyl-L-glutamic acid); and maleic anhydride copolymers (e.g., styrene-maleic acid copolymers).

The mode of monomer binding may be random, block, or graft. When the above-mentioned α-hydroxymonocarboxylic acids, α-hydroxydicarboxylic acids, and α-hydroxytricarboxylic acids have an optically active center in their molecular structures, they may be of the D-, L-, or DL-configuration. Of these, lactic acid-glycolic acid polymers [hereinafter also referred to as poly(lactide-co-glycolide), poly(lactic acid-co-glycolic acid) or lactic acid-glycolic acid copolymer; generically refer to lactic acid-glycolic acid homopolymers and copolymers, unless otherwise specified; lactic acid homopolymers are also referred to as lactic acid polymer, polylactic acids, polylactides etc., and glycolic acid homopolymers as glycolic acid polymers, polyglycolic acids, polyglycolides etc.], with preference given to poly(α-cyanoacrylic esters) etc. Greater preference is given to lactic acid-glycolic acid polymers. More preferably, lactic acid-glycolic acid polymers having a free carboxyl group at one end are used.

The biodegradable polymer may be a salt. Salts include, for example, salts with inorganic bases (e.g., alkali metals such as sodium and potassium, alkaline earth metals such as calcium and magnesium), organic bases (e.g., organic amines such as triethylamine, basic amino acids such as arginine), and salts and complex salts with transition metals (e.g., zinc, iron, copper).

When the biodegradable polymer used is a lactic acid-glycolic acid polymer, the content ratio (mol %) is preferably about 100/0 to about 40/60, more preferably about 100/0 to about 50/50. Lactic acid homopolymers having a content ratio of 100/0 are also preferably used.

The optical isomer ratio of lactic acid, one of the minimum repeat units for said lactic acid-glycolic acid polymer is preferably between about 75/25 and about 25/75, as of the D-configuration/L-configuration ratio (mol/mol %). Lactic acid-glycolic acid polymers having a D-configuration/L-configuration ratio (mol/mol %) between about 60/40 and about 30/70 are commonly used.

The weight-average molecular weight of said lactic acid-glycolic acid polymer is normally about 3,000 to about 100,000, preferably about 3,000 to about 60,000, more preferably about 3,000 to about 50,000, and still more preferably about 20,000 to about 50,000.

The degree of dispersion (weight-average molecular weight/number-average molecular weight) is normally about 1.2 to about 4.0, more preferably about 1.5 to 3.5.

The free carboxyl group content of said lactic acid-glycolic acid polymer is preferably about 20 to about 1,000 µmol, more preferably about 40 to about 1,000 µmol, per unit mass (gram) of the polymer.

Weight-average molecular weight, number-average molecular weight and degree of dispersion, as defined herein, are polystyrene-based molecular weights and degree of dispersion determined by gel permeation chromatography (GPC) with 15 polystyrenes as reference substances with weight-average molecular weights of 1,110,000, 707,000, 455,645, 354,000, 189,000, 156,055, 98,900, 66,437, 37,200, 17,100, 9,830, 5,870, 2,500, 1,303, and 504, respectively. Measurements were taken using a high-speed GPC device (produced by Toso, HLC-8120GPC, detection: Refractory Index) and a GPC column KF804Lx2 (produced by Showa Denko), with chloroform as a mobile phase.

The term free carboxyl group content, as used herein, is defined to be obtained by the labeling method (hereinafter referred to as "carboxyl group content as determined by the labeling method"). Specific procedures for determining this content in a polylactic acid are described below. First, W mg of the polylactic acid is dissolved in 2 ml of a 5 N hydrochloric acid/acetonitrile (v/v=4/96) mixture; 2 ml of a 0.01 M solution of o-ni-trophenylhydrazine hydrochloride (ONPH) (5 N hydrochloric acid/acetonitrile/ethanol=1.02/35/15) and 2 ml of a 0.15 M solution of 1-ethyl-3-(3-dimethylaminopropyl)-carbodiimide hydrochloride (pyridine/ethanol=4v/96v) were added, followed by a reaction at 40° C. for 30 minutes, after which the solvent is removed. After water washing (4 times), the residue is dissolved in 2 ml of acetonitrile; 1 ml of a 0.5 mol/l ethanolic solution of potassium hydroxide is added, followed by a reaction at 60° C. for 30 minutes. The reaction mixture is diluted with a 1.5 N aqueous solution of sodium hydroxide to Y ml; absorbance a (/cm) at 544 nm is determined, with a 1.5 N aqueous solution of sodium hydroxide as control. Separately, with an aqueous solution of DL-lactic acid as reference, its free carboxyl group content C mol/l is determined by alkali titration. Taking the absorbance at 544 nm of the DL-lactic acid hydrazide prepared by the ONPH labeling method as B (/cm), the molar content of the free carboxyl groups per unit mass (gram) of the polymer can be calculated using the equation: [COOH] (mol/g)=(AYC)/(WB)

Although said carboxyl group content can also be obtained by dissolving the biodegradable polymer in a toluene-acetone-methanol mixed solvent, and titrating this solution for carboxyl groups with an alcoholic solution of potassium hydroxide, with phenolphthalein as indicator (value obtained by this method hereinafter referred to as "carboxyl group content as determined by the alkali titration method"), it is desirable that quantitation be achieved by the labeling method described above, since it is possible that the titration endpoint is made unclear as a result of competition of the hydrolytic reaction of the polyester main chain during titration.

The decomposition/elimination rate of a biodegradable polymer varies widely, depending on copolymer composition, molecular weight or free carboxyl group content. However, drug release duration can be extended by lowering the glycolic acid ratio or increasing the molecular weight and lowering the free carboxyl group content, because decomposition/elimination is usually delayed as the glycolic acid ratio decreases, in the case of lactic acid-glycolic acid polymers. Because the free carboxyl group content affects the rate of bioactive substance incorporation in the preparation, however, it must be above a given level. For this reason, it is preferable, in obtaining a biodegradable polymer for a sustained-release preparation of the long acting type (e.g., 6 months or longer), that in the case of a lactic acid-glycolic acid polymer, a polylactic acid (e.g., D-lactic acid, L-lactic acid, DL-lactic acid, preferably DL-lactic acid etc.) whose weight-average molecular weight and free carboxyl group content as determined as described above are about 20,000 to about 50,000 and about 30 to about 95 µmol/g, preferably about 40 to about 95 µmol/g, more preferably about 50 to about 90 µmol/g, be used.

Said "lactic acid-glycolic acid polymer" can be produced by, for example, the catalyst-free dehydration polymerization condensation method (Japanese Patent Unexamined Publication No. 28521/1986) from a lactic acid and a glycolic acid, or ring-opening polymerization from a lactide and a cyclic diester compound such as glycolide by means of a catalyst (Encyclopedic Handbook of Biomaterials and Bioengineering Part A: Materials, Volume 2, Marcel Dekker, Inc., 1995). Although the polymer obtained by the above-mentioned known method of ring-opening polymerization does not always contain a free carboxyl group at one end, it can also be used after being modified to a polymer having a given amount of carboxyl groups per unit mass, by subjecting it to the hydrolytic reaction described in EP-A-0839525.

The above-described "lactic acid-glycolic acid polymer having a free carboxyl group at one end" can be produced, with no problem, by a commonly known method (e.g., catalyst-free dehydration polymerization condensation, Japanese Patent Unexamined Publication No. 28521/1986), or by the method described below.

(1) First, in the presence of a hydroxymonocarboxylic acid derivative (e.g., tert-butyl D-lactate, benzyl L-lactate) with its carboxyl group protected, or a hydroxydicarboxylic acid derivative (e.g., dibenzyl tartronate, di-tert-butyl 2-hydroxyethylmalonate) with its carboxyl group protected, a cyclic ester compound is subjected to a polymerization reaction using a polymerization catalyst.

The above-described "hydroxymonocarboxylic acid derivative with its carboxyl group protected" or "hydroxydicarboxylic acid derivative with its carboxyl group protected" is exemplified by hydroxycarboxylic acid derivatives with its carboxyl group (—COOH) amidated (—CONH$_2$) or esterified (—COOR), with preference given to hydroxycarboxylic acid derivatives with its carboxyl group (—COOH) esterified (—COOR) etc.

Here, R for the ester is exemplified by $C_{1-6}$ alkyl groups such as methyl, ethyl, n-propyl, isopropyl, n-butyl, and tert-butyl, $C_{3-8}$ cycloalkyl groups such as cyclopentyl and cyclohexyl, $C_{6-12}$ aryl groups such as phenyl and α-naphthyl, and $C_{7-14}$ aralkyl groups such as phenyl-$C_{1-2}$ alkyl groups such as benzyl and phenethyl, and α-naphthyl-$C_{1-2}$ alkyl groups such as α-naphthylmethyl. Of these groups, tert-butyl groups, benzyl groups etc. are preferred.

Said "cyclic ester compound" refers to a cyclic compound having at least one ester linkage in the ring thereof. Specifically, such compounds include cyclic monoester compounds (lactones) or cyclic diester compounds (lactides).

Said "cyclic monoester compound" is exemplified by 4-membered ring lactones (β-propiolactone, β-butyrolactone, β-isovalerolactone, β-caprolactone, β-isocaprolactone, β-methyl-β-valerolactone etc.), 5-membered ring lactones (γ-butyrolactone, γ-valerolactone etc.), 6-membered ring lactones (δ-valerolactone etc.), 7-membered ring lactones (ε-caprolactone etc.), p-dioxanone, and 1,5-dioxepan-2-one.

Said "cyclic diester compound" is exemplified by the compounds represented by the formula:

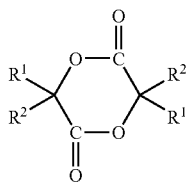

Wherein $R^1$ and $R^2$, whether identical or not, represent a hydrogen atom or a $C_{1-6}$ alkyl group such as methyl, ethyl, n-propyl, isopropyl, n-butyl, or tert-butyl), with preference given to the lactides having a hydrogen atom for $R^1$ and a methyl group for $R^2$, or having a hydrogen atom for $R^1$ and $R^2$, etc.

Specifically, such compounds include glycolides, L-lactides, D-lactides, DL-lactides, meso-lactides, and 3-methyl-1,4-dioxane-2,5-dione (including optically active configurations).

Said "polymerization catalyst" is exemplified by organic tin catalysts (e.g., tin octylate, di-n-butyltin di-laurylate, tetraphenyltin), aluminum catalysts (e.g., triethylaluminum), and zinc catalysts (e.g., diethylzinc).

From the viewpoint of ease of removal after reaction, aluminum catalysts and zinc catalysts are preferred; from the viewpoint of safety in case of retention, zinc catalysts are preferred.

Useful solvents for polymerization catalysts include benzene, hexane, and toluene, with preference given to hexane, toluene etc.

Regarding "method of polymerization," the mass polymerization method, which is conducted with the reaction product in a molten state, or the solution polymerization method, which is conducted with the reaction product dissolved in an appropriate solvent (e.g., benzene, toluene, xylene, decalin, dimethylformamide). Although polymerization temperature is not limited, it is not lower than the temperature at which the reaction product becomes molten at reaction initiation, normally 100 to 300° C., for mass polymerization, and is normally room temperature to 150° C. for solution polymerization; if the reaction temperature exceeds the boiling point of the reaction solution, the reaction is carried out under refluxing using a condenser or in a pressure-resistant reactor. Determined as appropriate in consideration of polymerization temperature, other reaction conditions, physical properties of the desired polymer, etc., polymerization time is, for example, 10 minutes to 72 hours. After completion of the reaction, polymerization is terminated with an acid (e.g., hydrochloric acid, acetic anhydride, trifluoroacetic acid), with the reaction mixture dissolved in an appropriate solvent (e.g., acetone, dichloromethane, chloroform) if necessary, after which the mixture is mixed in a solvent that does not dissolve the desired product (e.g., alcohol, water, ether, isopropyl ether) or otherwise precipitated, followed by the isolation of a polymer having a protected carboxyl group at the ω-end.

The method of polymerization of the present application employs hydroxycarboxylic acid derivatives (e.g., tert-butyl D-lactate, benzyl L-lactate) with a protected carboxyl group or hydroxydicarboxylic acid derivatives (e.g., dibenzyl tartronate, di-tert-butyl L-2-hydroxyethylmalonate) with a protected carboxyl, in place of conventional protonic chain transferring agents such as methanol.

Using hydroxycarboxylic acid derivatives (e.g., tert-butyl D-lactate, benzyl L-lactate) with a protected carboxyl group or hydroxydicarboxylic acid derivatives (e.g., dibenzyl tartronate, di-tert-butylL-2-hydroxyethylmalonate) with a protected carboxyl, as protonic chain transferring agents, it is possible to ① achieve molecular weight control by the composition of the starting materials, and to ② liberate the carboxyl group at the ω-end of the biodegradable polymer obtained, by a deprotection reaction after polymerization.

(2) Second, by subjecting the polymer obtained by the polymerization reaction described in paragraph (1) above, which has a protected carboxyl group at the ω-end, to a deprotection reaction, the desired biodegradable polymer having a free carboxyl group at the ω-end can be obtained.

Said protecting group can be removed by commonly known methods. Such methods include all methods enabling the removal of the protecting group without affecting the ester linkage of poly(hydroxycarboxylic acid), specifically exemplified by reduction and acid decomposition.

Such methods of reduction include, for example, catalytic reduction using catalysts (e.g., palladium carbon, palladium black, platinum oxide), reduction using sodium in liquid ammonium, and reduction with dithiothreitol. When a polymer having a protected carboxyl group at the ω-end is subjected to catalytic reduction, for example, deprotection can be achieved by adding palladium carbon to a solution of the polymer in ethyl acetate, dichloromethane, chloroform, or the like, and supplying hydrogen at room temperature for about 20 minutes to about 4 hours with vigorous shaking.

Such methods of acid decomposition include, for example, acid decomposition with inorganic acids (e.g., hydrogen fluoride, hydrogen bromide, hydrogen chloride), organic acids (e.g., trifluoroacetic acid, methanesulfonic acid, trifluoromethanesulfonic acid), or mixtures thereof. Also, where necessary, a cation scavenger (e.g., anisole, phenol, thioanisole) is added as appropriate. When a polymer having a carboxyl group protected with a tert-butyl group, at the ω-end, is subjected to acid decomposition, for example, deprotection can be achieved by adding an appropriate amount of trifluoroacetic acid to a solution of the polymer in dichloromethane, xylene, toluene, or the like, or dissolving the polymer in trifluoroacetic acid, and stirring at room temperature for about 1 hour.

Preferably, said acid decomposition is conducted just after the polymerization reaction; in this case, it can serve as a polymerization termination reaction.

Furthermore, by subjecting the polymer obtained by the above-described deprotection reaction to an acid hydrolytic reaction as necessary, the weight-average molecular weight, number-average molecular weight or terminal carboxyl group content of said polymer can be regulated according to the purpose. Specifically, this can, for example, be achieved by the method described in EP-A-0839525 or a method based thereon.

A biodegradable polymer obtained as described above can be used as a base for producing a sustained-release preparation.

In addition, a polymer having a given free carboxyl group at one end can be produced by known production methods (e.g., see Patent Publication for WO94/15587).

Also, a lactic acid-glycolic acid polymer with one end rendered a free carboxyl group by a chemical treatment after ring-opening polymerization may be a commercial product of Boehringer Ingelheim KG, for example.

The biodegradable polymer may be a salt (salts of biodegradable polymers include, for example, the salts mentioned above). Useful methods of their production include, for example, (a) the method in which a solution of the above-described biodegradable polymer having a carboxyl group in an organic solvent, and an aqueous solution containing the ions of inorganic bases (e.g., alkali metals such as sodium and potassium, alkaline earth metals such as calcium and magnesium) or organic bases (e.g., organic amines such as triethylamine, basic amino acids such as arginine), are mixed together to cause an ion exchange reaction, after which the polymer, now in the form of a salt, is isolated, (b) the method in which a weak acid salt (e.g. acetate, glycolate) of a base listed in (a) above is dissolved in a solution of the above-described biodegradable polymer having a carboxyl group in an organic solvent, after which the polymer, now in the form of a salt, is isolated, and (c) the method in which a weak acid salt (e.g. acetate, glycolate) or oxide of a transition metal (e.g., zinc, iron, copper) is mixed in a solution of the above-described biodegradable polymer having a carboxyl group in an organic solvent, after which the polymer, now in the form of a salt, is isolated.

As a biodegradable polymer for a sustained-release preparation of the long acting type (e.g., 6 months or longer), the "lactic acid-glycolic acid polymer having a free carboxyl group at one end" produced by the method described above is preferred.

The ratio by weight of the bioactive substance in the composition of the present invention varies depending on kind of bioactive substance, desired pharmacological effect, duration of effect, and other factors. In the case of a sustained-release composition containing three components (bioactive substance or salt thereof, hydroxynaphthoic acid or salt thereof, and biodegradable polymer or salt thereof), the ratio by weight of bioactive peptide or salt thereof, for example, is about 0.001 to about 50% by weight, preferably about 0.02 to about 40% by weight, more preferably about 0.1 to 30% by weight, and most preferably about 14 to 24% by weight, relative to the sum of the three components. In the case of a non-peptide bioactive substance or salt thereof, the ratio is about 0.01 to 80% by weight, preferably about 0.1 to 50% by weight. When the hydroxynaphthoic acid salt of a bioactive substance is contained, similar ratios by weight are applicable. In the case of a sustained-release composition containing the salt of a bioactive peptide (referred to as (A)) with hydroxynaphthoic acid (referred to as (B)), the ratio by weight of (A) is normally about 5 to about 90% by weight, preferably about 10 to about 85% by weight, more preferably about 15 to about 80% by weight, and still more preferably about 30 to about 80% by weight, relative to the sum of the salt (A) with (B).

In the case of a sustained-release composition containing three components (bioactive substance or salt thereof, hydroxynaphthoic acid or salt thereof, and biodegradable polymer or salt thereof), the amount of hydroxynaphthoic acid or salt thereof formulated is preferably about 1/2 to about 2 mol, more preferably about 3/4 to about 4/3 mol, and still more preferably about 4/5 to about 6/5 mol, per mol of bioactive substance or salt thereof.

Designing the composition of the present invention is hereinafter described for a sustained-release composition containing three components: basic bioactive substance, hydroxynaphthoic acid, and biodegradable polymer. In this case, the bioactive substance, as a base, and hydroxynaphthoic acid, as an acid, are concurrently present in the composition; whether they are formulated in the composition in the form of free configurations or salts, a dissociation equilibrium for each component is present, in a hydrated state, or in the presence of a trace amount of water, at a point during production of the composition. Because the salt formed by any hydroxynaphthoic acid, which is very slightly soluble in water, with a bioactive substance is assumed to be very slightly soluble in water, although the solubility also depends on the characteristics of said bioactive substance, its dissociation equilibrium shifts toward the formation of a salt very slightly soluble in water.

In producing a composition having high contents of a basic bioactive substance, it is desirable that most of the bioactive substance be protonated to render it to a salt very slightly soluble in water as described above, judging from the above-described dissociation equilibrium. For this purpose, it is desirable that the hydroxynaphthoic acid or salt thereof be formulated in an amount at least nearly equivalent to that of the bioactive substance or salt thereof.

Next, the mechanism of release of a bioactive sub-stance included in a composition is described below. In the above-described formula composition, the bioactive substance is mostly protonated and present with a counter ion. The counter ion is mainly hydroxynaphthoic acid (preferably hydroxynaphthoic acid). After the composition is administered to the living body, its oligomers and monomers begin to be produced over time due to decomposition of the biodegradable polymer. When said polymer is a lactic acid-glycolic acid polymer, the resulting oligomer (lactic acid-glycolic acid oligomer) and monomer (lactic acid or glycolic acid) always has one carboxyl group, which can also serve as a counter ion for the bioactive substance. The bioactive substance is released without charge transfer, or in the form of a salt with a counter ion; transferable counter ions include hydroxynaphthoic acids, lactic acid-glycolic acid oligomers (of such molecular weights that transfer is possible), and monomers (lactic acid or glycolic acid), as described above.

When a plurality of acids are concurrently present, salts of stronger acids are usually preferentially produced, although the outcome also depends on their content ratio. Regarding the pKa values of hydroxynaphthoic acids, 3-hydroxy-2-naphthoic acid, for example, is known to have a pKa value of 2.708 (Kagaku Binran Kisohen II, Chemical Society of Japan, published Sep. 25, 1969). On the other hand, the pKa values of the carboxyl groups of lactic acid-glycolic acid oligomers are unknown but can be calculated on the basis of the pKa value of lactic acid or glycolic acid (=3.86 or 3.83), in accordance with the theory that "the free energy level change due to substituent introduction can be approximated by the addition rule." The contributions of substituents to dissociation constants have already been determined and can be used for this purpose (Table 4.1 in "pKa Prediction for Organic Acid and Bases," D. D. Perrin, B. Dempsey, and E. P. Serjeant, 1981). Because the following data are applicable for the hydroxyl group and ester linkage:

$\Delta pKa\ (OH) = -0.90$ $\Delta pKa\ (ester\ linkage) = -1.7$ the pKa value of the carboxyl group of lactic acid-glycolic acid oligomers can be determined, in consideration of the contribution of the ester linkage closest to the dissociation group, as follows:

$pKa = pKa$ (lactic acid or glycolic acid) $-\Delta pKa\ (OH) + \Delta pKa$ (ester linkage) $= 3.06$ or $3.03$ Because hydroxynaphthoic acids are therefore stronger acids than lactic acid (pKa=3.86), glycolic acid (pKa=3.83), and lactic acid-glycolic acid oligomers, it is assumed that the hydroxynaphthoic acid salt of the bioactive substance is preferentially produced in the above-described composition, the characteristics of the salt being assumed to predominantly determine the nature of sustained-release of the bioactive substance from the composition. Said bioactive substance is exemplified by the bioactive substances described above.

Here, the fact that the salt formed by the hydroxynaphthoic acid with the bioactive substance is very slightly soluble in water, rather than insoluble in water, serves in favor of the sustained-release mechanism. In other words, as demonstrated in the above discussion of acid dissociation constant, the salt of hydroxynaphthoic acid, a stronger acid than the above-described lactic acid-glycolic acid oligomers and monomers, is predominant in the initial stage of release; the initial release pattern of the drug can be regulated by the content ratio of hydroxynaphthoic acid, because the solubility and body tissue distribution profile of the salt serves as determinants of the bioactive substance release rate. Then, as the oligomers and monomers increase, due to reduction in the hydroxynaphthoic acid and hydrolysis of the biodegradable polymer, the bioactive substance release mechanism involving oligomers and monomers as counter ions becomes predominant gradually; even if the hydroxynaphthoic acid disappears substantially from said "composition," stable bioactive substance release is achieved. The increased efficiency of bioactive substance incorporation for production of a sustained-release composition, and the possibility of suppression of initial burst after administration of the bioactive substance incorporated, can also be explained.

The role of the hydroxynaphthoic acid in the sustained-release composition containing the hydroxynaphthoic acid salt of a bioactive peptide can also be explained by the above-described mechanism.

The term "insoluble in water," as used herein, means that when said substance is stirred in distilled water for 4 hours at temperatures of not higher than 40° C., the mass of the substance that dissolves in 1 l of the solution is not more than 25 mg.

The term "very slightly soluble in water," as used herein, means that the above-described mass is not less than 25 mg and not more than 5 g. When said substance is a salt of a bioactive substance, the above definition is applied for the mass of the bioactive substance that dissolved in the above-described operation.

Although the sustained-release composition of the present invention is not subject to limitation as to form, microparticles are preferred, with greater preference given to microspheres (also referred to as microcapsules in the case of sustained-release compositions containing biodegradable polymers). The term "microsphere," as used herein, is defined as an injectable sphere that can be dispersed in solutions. Its shape can be confirmed by, for example, scanning microscopy.

MODES OF EMBODIMENT OF THE INVENTION

Production methods for sustained-release compositions of the present invention, which contain a biologically active substance or a salt thereof, a hydroxynaphthoic acid or a salt thereof, and a biodegradable polymer or a salt thereof, microspheres, are exemplified below.

(I) Water-in Drying Method (i) O/W Method

In this method, an organic solvent solution of the hydroxynaphthoic acid or a salt thereof and biodegradable polymer or a salt thereof is prepared.

Said organic solvent is exemplified by halogenated hydrocarbons (e.g., dichloromethane, chloroform, dichloroethane, trichloroethane, carbon tetrachloride), ethers (e.g., ethyl ether, isopropyl ether), fatty acid esters (e.g., ethyl acetate, butyl acetate), aromatic hydrocarbons (e.g., benzene, toluene, xylene), alcohols (e.g., ethanol, methanol), and acetonitrile. Among these, dichloromethane is preferable for an organic solvent of the biodegradable polymer or a salt thereof. Alcohols are preferable for an organic solvent of the hydroxynaphthoic acid or a salt thereof. These solvents may be used in mixtures at appropriate ratios. Of these solvents, mixtures of halogenated hydrocarbons and alcohols are preferred, with greater preference given to mixtures of dichloromethane and ethanol.

When the organic solvent used is a mixture of dichloromethane and ethanol, the ratio of their concentrations is normally chosen over the range from about 0.01 to about 50% (v/v), preferably from about 0.05 to about 40% (v/v), and more preferably from about 0.1 to about 30% (v/v).

The biodegradable polymer concentration in the organic solvent solution varies depending on the molecular weight of biodegradable polymer and the kind of organic solvent. For example, when the organic solvent used is dichloromethane, the biodegradable polymer concentration is normally chosen over the range from about 0.5 to about 70% by weight, preferably from about 1 to about 60% by weight, and more preferably from about 2 to about 50% by weight.

The hydroxynaphthoic acid or a salt thereof concentration in the organic solvent solution is normally chosen, for example, over the range from about 0.01 to about 10% by weight, preferably from about 0.1 to about 5% by weight, and more preferably from about 0.5 to about 3% by weight.

The biologically active substance or salt thereof is added to thus-obtained organic solvent solution containing a hydroxynaphthoic acid or salt thereof, and a biodegradable polymer, and dissolved or dispersed.

The thus-obtained organic solvent solution containing a biologically active substance or salt thereof, a hydroxynaphthoic acid or salt thereof, and a biodegradable polymer, is then added to a water phase to form an O (oil phase)/W (water phase) emulsion, after which the solvent is evaporated from the oil phase to yield microspheres.

For this operation, the water phase volume is normally chosen over the range from about 1 time to about 10,000 times, preferably from about 5 times to about 50,000 times, and more preferably from about 10 times to about 2,000 times, the oil phase volume.

An emulsifier may be added to the above-described external water phase. Said emulsifier may be any one, as long as it is capable of forming a stable O/W emulsion. Such emulsifiers include, for example, anionic surfactants (e.g., sodium oleate, sodium stearate, sodium lauryl sulfate), non-ionic surfactants [e.g., polyoxyethylene sorbitan fatty acid esters (Tween 80, Tween 60, Atlas Powder Company), polyoxyethylene castor oil derivatives (e.g., HCO-60, HCO-50, Nikko Chemicals)], polyvinylpyrrolidone, polyvinyl alcohol, carboxymethyl cellulose, lecithin, gelatin and hyaluronic acid. These emulsifiers may be used singly or in combination. Regarding the concentration, it is preferable that they be used over the range from about 0.01% to 10% by weight, preferably from about 0.05% to about 5% by weight.

An osmotic pressure regulator may be added to the above-described external water phase. Said osmotic pressure regulator may be any one, as long as it shows an osmotic pressure when prepared as an aqueous solution.

Said osmotic pressure regulator is exemplified by polyhydric alcohols, monohydric alcohols, monosaccharides, disaccharides, oligosaccharides, amino acids, and derivatives thereof.

Useful polyhydric alcohols include, for example, dihydric alcohols such as glycerol, pentahydric alcohols such as arabitol, xylitol and adonitol, and hexahydric alcohols such as mannitol, sorbitol and dulcitol. Of these alcohols, hexavalent alcohols are preferred, with greater preference given to mannitol.

Useful monohydric alcohols include, for example, methanol, ethanol and isopropyl alcohol, with preference given to ethanol.

Useful monosaccharides include, for example, pentoses such as arabinose, xylose, ribose and 2-deoxyribose, and hexoses such as glucose, fructose, galactose, mannose, sorbose, rhamnose and fucose, with preference given to pentoses.

Useful oligosaccharides include, for example, trisaccharides such as maltotriose and raffinose, and tetrasaccharides such as stachyose, with preference given to trisaccharides.

Useful derivatives of monosaccharides, disaccharides and oligosaccharides include, for example, glucosamine, galactosamine, glucuronic acid and galacturonic acid.

Useful amino acids include, for example, glycine, leucine and arginine, with preference given to L-arginine.

These osmotic pressure regulators may be used singly, or in combination.

These osmotic pressure regulators are normally used at such concentrations that the external water phase osmotic pressure is about 1/50 to about 5 times, preferably about 1/25 to about 3 times, the physiological saline osmotic pressure.

Organic solvent removal can be achieved by commonly known methods or methods based thereon. Such methods include, for example, the method in which the organic solvent is evaporated under normal or gradually reduced pressure during stirring using a propeller stirrer, magnetic stirrer or the like, and the method in which the organic solvent is evaporated while the degree of vacuum is adjusted using a rotary evaporator or the like.

The thus-obtained microspheres are centrifuged or filtered to separate them, after which they are washed with distilled water several times to remove the free biologically active substance, hydroxynaphthoic acid, drug support, emulsifier etc. adhering to the microsphere surface, then again dispersed in distilled water etc. and freeze-dried.

To prevent mutual aggregation of particles during the production process, an anticoagulant may be added. Said anticoagulant is exemplified by water-soluble polysaccharides such as mannitol, lactose, glucose and starches (e.g., corn starch), amino acids such as glycine, and proteins such as fibrin and collagen. Of these substances, mannitol is preferred.

Where necessary, freeze-drying may be followed by heating under reduced pressure without causing mutual adhesion of microspheres, to remove the water and organic solvent from the microspheres. It is preferable that the microspheres be heated at a temperature slightly higher than the intermediate glass transition point of the biodegradable polymer, as determined using a differential scanning calorimeter when the temperature is increased at a rate of 10 to 20° C. per minute. More preferably, the microspheres are heated within the temperature range from the intermediate glass transition point of the biodegradable polymer to a temperature higher by about 30° C. than the glass transition temperature. When a lactic acid-glycolic acid polymer is used as the biodegradable polymer, in particular, it is preferable that the microspheres be heated within the temperature range from the intermediate glass transition point to a temperature higher by 10° C. than the glass transition temperature, more preferably within the temperature range from the intermediate glass transition point to a temperature higher by 5° C. than the glass transition temperature.

Although it varies depending on the amount of microspheres and other factors, heating time is normally about 12 hours to about 168 hours, preferably about 24 hours to about 120 hours, and more preferably about 48 hours to about 96 hours, after the microspheres reach a given temperature.

Any heating method can be used, as long as microsphere aggregates are uniformly heated.

Useful thermal drying methods include, for example, the method in which thermal drying is conducted in a constant-temperature chamber, fluidized bed chamber, mobile chamber or kiln, and the method using microwaves for thermal drying. Of these methods, the method in which thermal drying is conducted in a constant-temperature chamber is preferred.

(ii) W/O/W Method (1)

First, an organic solvent solution containing a biodegradable polymer or salt thereof is prepared.

The concentration of the organic solvent and the biodegradable polymer or salt thereof are the same as those described in paragraph (I) (i) above.

When more than two kinds of solvents are used, the ratios of these solvents are the same as those described in paragraph (I) (i) above. The biologically active substance or salt thereof is added to thus-obtained organic solvent solution containing the biodegradable polymer, then dissolved and dispersed.

Next, to the organic solvent solution (oil phase) of the biologically active substance and biodegradable polymer, a solution of a hydroxynaphthoic acid or salt thereof [this solvent exemplified by water, alcohols (e.g., methanol, ethanol), pyridine solution, dimethylacetamide solution etc.] is added. This mixture is emulsified by a known method such as homogenization or sonication to form a W/O emulsion.

The thus-obtained W/O emulsion containing a biologically active substance or salt thereof, hydroxynaphthoic acid or salt thereof, and a biodegradable polymer or salt thereof, is then added to a water phase to form a W (internal water phase)/O (oil phase)/W (external water phase) emulsion, after which the solvent is evaporated from the oil phase to yield microspheres. For this operation, the external water phase volume is normally chosen over the range from about 1 time to about 10,000 times, preferably from about 5 times to about 50,000 times, and more preferably from about 10 times to about 2,000 times, the oil phase volume.

The above-described emulsifier and osmotic pressure regulator that may be added to the external water phase, and the subsequent procedures are the same as those described in paragraph (I) (i) above.

(ii) W/O/W Method (2)

First, an organic solvent solution containing a hydroxynaphthoic acid and a biodegradable polymer is prepared. Thus-obtained organic solvent solution is referred to as an oil phase. The preparation method is the same as those described in paragraph (I)(i) above.

Alternatively, an organic solvent solution containing a hydroxynaphthoic acid and an organic solvent solution containing a biodegradable polymer may be prepared separately, and mixed together to prepare the oil phase.

The biodegradable polymer concentration in the organic solvent solution varies depending on the molecular weight of biodegradable polymer and the kind of organic solvent. For example, when the organic solvent used is dichloromethane, the biodegradable polymer concentration is normally chosen over the range from about 0.5 to about 70% by weight, preferably from about 1 to about 60% by weight, and more preferably from about 2 to about 50% by weight.

Next, a solution of a biologically active substance or salt thereof [this solvent exemplified by water, alcohols (e.g., methanol, ethanol)], is prepared. Thus-obtained solution is referred to as internal water phase. The concentration of the biologically active substance is normally 0.001 mg/ml to 10 g/ml, preferably 0.1 mg/ml to 5 g/ml, more preferably 10 mg/ml to 3 g/ml. The oil phase and the internal water phase are emulsified by a known method such as homogenization or sonication to form a W/O emulsion.

For this operation, the oil phase volume is normally chosen over the range from about 1 time to about 1,000 times, preferably from about 2 times to about 100 times, and more preferably from about 3 times to about 10 times, the internal water phase volume.

The viscosity of the w/o emulsion is normally chosen over the range from about 10 to about 1,0000 cp, preferably from about 100 to about 5,000 cp, more preferably from about 500 to about 2,000 cp.

Thus-obtained W/O emulsion containing a biologically active substance or salt thereof, hydroxynaphthoic acid or salt thereof, and a biodegradable polymer, is then added to a water phase to form a w(internal water phase)/o(oil phase)/w(external water phase) emulsion, after which the solvent is evaporated from the oil phase to yield microspheres. For this operation, the external water phase volume is normally chosen over the range from about 1 time to about 10,000 times, preferably from about 2 times to about 100 times, and more preferably from about 3 times to about 10 times, the internal water phase volume.

The above-described emulsifier and osmotic pressure regulator that may be added to the external water phase, and the subsequent procedures are the same as those described in paragraph (I) (i) above.

(II) Phase Separation Method

For producing microspheres by this method, a coacervating agent is added little by little to the organic solvent solution described in aqueous drying method paragraph (I) above, which contains a composition consisting of a biologically active substance or salt thereof, hydroxynaphthoic acid or salt thereof and biodegradable polymer or salt thereof, during stirring, to precipitate and solidify the microspheres. Said coacervating agent is added in an amount by volume of about 0.01 to 1,000 times, preferably about 0.05 to 500 times, and more preferably about 0.1 to 200 times, the oil phase volume.

Said coacervating agent may be any one, as long as it is a polymer, mineral oil or vegetable oil compound that is miscible in the organic solvent, and that does not dissolve the salt complex of the biologically active substance with the hydroxynaphthoic acid and biocompatible polymer. Specifically, useful coacervating agents include, for example, silicon oil, sesame oil, soybean oil, corn oil, cotton seed oil, coconut oil, linseed oil, mineral oil, n-hexane and n-heptane. These may be used in combination.

The microspheres thus obtained are collected, after which they are repeatedly washed with heptane etc. to remove the coacervating agent etc. other than the composition of the biologically active substance, hydroxynaphthoic acid and biodegradable polymer, followed by drying under reduced pressure. Alternatively, the microspheres are washed in the same manner as in aqueous drying method paragraph (I) (i) above, then freeze-dried and thermally dried.

(III) Spray Drying Method

For producing microspheres by this method, the organic solvent solution described in aqueous drying method paragraph (I) above, which contains a composition consisting of a biologically active substance or salt thereof, hydroxynaphthoic acid or salt thereof and biodegradable polymer or salt thereof, is sprayed via a nozzle into the drying chamber of a spray drier to volatilize the organic solvent in the fine droplets in a very short time, to yield microspheres. Said nozzle is exemplified by the double-fluid nozzle, pressure nozzle and rotary disc nozzle. The microspheres may be then freeze-dried and thermally dried as necessary after being washed in the same manner as that described in aqueous drying method paragraph (I) above.

For a dosage form other than the above-described microspheres, the organic solvent solution described in aqueous drying method paragraph (I) above, which contains a composition consisting of a biologically active substance or salt thereof, hydroxynaphthoic acid or salt thereof and biodegradable polymer or salt thereof, may be dried by evaporating the organic solvent and water, while the degree of vacuum is adjusted using a rotary evaporator or the like, followed by milling with a jet mill or the like, to yield microparticles.

The milled microparticles may be then freeze-dried and thermally dried after being washed in the same manner as that described in aqueous drying method paragraph (I) for microsphere production.

The microspheres or microparticles thus obtained enable drug release corresponding to the rate of decomposition of the biodegradable polymer or lactic acid-glycolic acid polymer used.

(IV) Two-Step Method

A biologically active substance or salt thereof is added to a solution of a hydroxynaphthoic acid or salt thereof in an organic solvent to a weight ratio falling within the above-described content range for biologically active substances, to yield an organic solvent solution of the hydroxynaphthoic acid of the biologically active substance.

Said organic solvent is the same as those described in paragraph (I)(i) above. When more than two kinds of organic solvents are used as a mixed solvent, the ratio of mixture is the same as those described in paragraph (I)(i) above.

Organic solvent removal for precipitation of a composition of a hydroxynaphthoic acid of the biologically active substance can be achieved by commonly known methods or methods based thereon. Such methods include, for example, the method in which the organic solvent is evaporated while the degree of vacuum is adjusted using a rotary evaporator or the like.

The thus-obtained composition of a hydroxynaphthoic acid of the biologically active substance can be again dissolved in an organic solvent to yield a sustained-release composition (microspheres or microparticles).

Said organic solvent is exemplified by halogenated hydrocarbons (e.g., dichloromethane, chloroform, dichloroethane, trichloroethane, carbon tetrachloride), ethers (e.g., ethyl ether, isopropyl ether), fatty acid esters (e.g., ethyl acetate, butyl acetate), and aromatic hydrocarbons (e.g., benzene, toluene, xylene). These solvents may be used in mixtures at appropriate ratios. Of these solvents, halogenated hydrocarbons are preferred, with greater preference given to dichloromethane.

The organic solvent solution containing the hydroxynaphthoic acid of the biologically active substance is then added to a water phase to form an O (oil phase)/W (water phase) emulsion, after which the solvent is evaporated from the oil phase to yield microspheres. For this operation, the water phase volume is normally chosen over the range from about 1 time to about 10,000 times, preferably from about 5 times to about 5,000 times, and more preferably from about 10 times to about 2,000 times, the oil phase volume.

An emulsifier, an osmotic pressure regulator, and the following step is the same as those described in paragraph (I) (i).

Organic solvent removal can be achieved by commonly known methods or methods based thereon. Such methods include, for example, the method in which the organic solvent is evaporated under normal or gradually reduced pressure during stirring using a propeller stirrer, magnetic stirrer or the like, and the method in which the organic solvent is evaporated while the degree of vacuum is adjusted using a rotary evaporator or the like.

The thus-obtained microspheres are centrifuged or filtered to separate them, after which they are washed with distilled water several times to remove the free biologically active substance, hydroxynaphthoic acid, emulsifier etc. adhering to the microsphere surface, then again dispersed in distilled water etc. and freeze-dried.

To prevent mutual aggregation of particles during the production process, an anticoagulant may be added. Said anticoagulant is exemplified by water-soluble polysaccharides such as mannitol, lactose, glucose and starches (e.g., corn starch), amino acids such as glycine, and proteins such as fibrin and collagen. Of these substances, mannitol is preferred.

Where necessary, freeze-drying may be followed by heating under reduced pressure without causing mutual adhesion of microspheres, to further remove the water and organic solvent from the microspheres.

Although it varies depending on the amount of microspheres and other factors, heating time is normally about 12 hours to about 168 hours, preferably about 24 hours to about 120 hours, and more preferably about 48 hours to about 96 hours, after the microspheres reach a given temperature.

Any heating method can be used, as long as microsphere aggregates are uniformly heated.

Useful thermal drying methods include, for example, the method in which thermal drying is conducted in a constant-temperature chamber, fluidized bed chamber, mobile chamber or kiln, and the method using microwaves for thermal drying. Of these methods, the method in which thermal drying is conducted in a constant-temperature chamber is preferred. The microspheres obtained are relatively uniformly spherical and undergo little resistance during administration by injection so that needle clogging is unlikely. Also, possible use of thin injection needles mitigates patient pain at injection.

(V) One-Step Method

A biologically active substance or salt thereof is added to a solution of a hydroxynaphthoic acid or salt thereof in an organic solvent to a weight ratio falling within the above-described content range for biologically active substances, to yield an organic solvent solution of the hydroxynaphthoic acid of the biologically active substance, after which a sustained-release preparation (microspheres or microparticles) is prepared.

Said organic solvent is the same as those described in (I) (i). When more than two organic solvents are used as mixed solvents, the ratio of mixture is as same as those described in (I) (i).

The organic solvent solution containing the hydroxynaphthoic acid of the biologically active substance is then added to a water phase to form an O (oil phase)/W. (water phase) emulsion, after which the solvent is evaporated from the oil phase to yield microspheres. For this operation, the water phase volume is normally chosen over the range from about 1 time to about 10,000 times, preferably from about 5 times to about 5,000 times, and more preferably from about 10 times to about 2,000 times, the oil phase volume.

The above-described emulsifier and osmotic pressure regulator that may be added to the external water phase, and the subsequent procedures are the same as those described in paragraph (IV) above.

The sustained-release composition of the present invention can be administered as such or in the form of various dosage forms prepared using it as a starting material, specifically as intramuscular, subcutaneous, visceral and other injectable preparations or implant preparations, nasal, rectal, uterine and other transdermal preparations, oral preparations [e.g., solid preparations such as capsules (e.g., hard capsules, soft capsules), granules and powders; liquids such as syrups, emulsions and suspensions] etc.

For example, the sustained-release composition of the present invention can be prepared as injectable preparations by suspending in water with a dispersing agent (e.g, surfactants such as Tween 80 and HCO-60, polysaccharides such as sodium hyaluronate, carboxymethyl cellulose and sodium alginate), a preservative (e.g., methyl paraben, propyl paraben), an isotonizing agent (e.g., sodium chloride, mannitol, sorbitol, glucose, proline) etc. to yield an aqueous suspension, or by dispersing in a vegetable oil such as sesame oil or corn oil to yield an oily suspension, whereby a practically useful sustained-release injectable preparation is obtained.

When the sustained-release composition of the present invention is used in the form of an injectable suspension, its particle diameter is chosen over such a range that the requirements concerning the degree of dispersion and needle passage are met. For example, the mean particle diameter normally ranges from about 0.1 to 300 µm, preferably from about 0.5 to 150 µm, and more preferably from about 1 to 100 µm.

The sustained-release composition of the present invention can be prepared as a sterile preparation by such methods in which the entire production process is aseptic, the method using gamma rays for sterilization, and the method in which a preservative is added, which methods are not to be construed as limitative.

Because of low toxicity, the sustained-release composition of the present invention can be used as a safe pharmaceutical etc. in mammals (e.g., humans, bovines, swines, dogs, cats, mice, rats, rabbits).

Although varying widely depending on kind, content and dosage form of the active ingredient biologically active substance, and duration of release of the biologically active substance, target disease, subject animal species and other factors, the dose of the sustained-release composition may be set at any level, as long as the biologically active substance is effective. The dose of the active ingredient biologically active substance per administration can be preferably chosen as appropriate over the range from about 0.01 mg to 10 mg/kg body weight, more preferably from about 0.05 mg to 5 mg/kg body weight, per adult in the case of a 1-month release preparation.

The dose of the sustained-release composition per administration can be preferably chosen as appropriate over the range from about 0.05 mg to 50 mg/kg body weight, more preferably from about 0.1 mg to 30 mg/kg body weight per adult.

The frequency of administration can be chosen as appropriate, depending on kind, content and dosage form of the active ingredient biologically active substance, duration of release of the biologically active substance, target disease, subject animal species and other factors, e.g., once every several weeks, one every month or once every several months (e.g., 3 months, 4 months, 6 months).

The sustained-release composition of the present invention is useful, depending on the biologically active substance which is contained in the sustained-release composition, as an agent for treating or preventing various kinds of diseases. When the biologically active substance is LH-RH derivatives, the sustained-release composition of the present invention is useful as an agent for treating or preventing of hormone-dependent diseases, especially sex hormone-dependent diseases, such as sex hormone-dependent cancer (e.g. prostatic cancer, hysterocarcinoma, breast cancer, hypophysoma, etc.), prostatic hypertrophy, endometriosis, hysteromyoma, precocious puberty, dysmenorrheal, amenorrhea, premenstrual syndrome, multilocular-ovary syndrome. The sustained-release composition of the present invention is also useful for an anticonceptive agent. When the rebound effect of after medication is used, the sustained-release composition of the present invention is useful as an agent for treating or preventing of infecundity. Further, the sustained-release composition of the present invention is useful as an agent for treating or preventing of sex hormone-nondependent, but LH-RH sensitive benign or cacoethic neoplasm.

EXAMPLES

The present invention is hereinafter described in more detail by means of the following examples, which are not to be construed as limitative.

Example 1

3,429.6 mg of the acetate (produced by TAP) of N—(S)-tetrahydrofur-2-oyl-Gly-D2Nal-D4ClPhe-D3 Pal-Ser-NMeTyr-DLys(Nic)-Leu-Lys(Nisp)-Pro-DAlaNH$_2$ (SEQ ID NO.: 4) (hereinafter referred to as peptide A)

(Chemical Formula of peptide A)

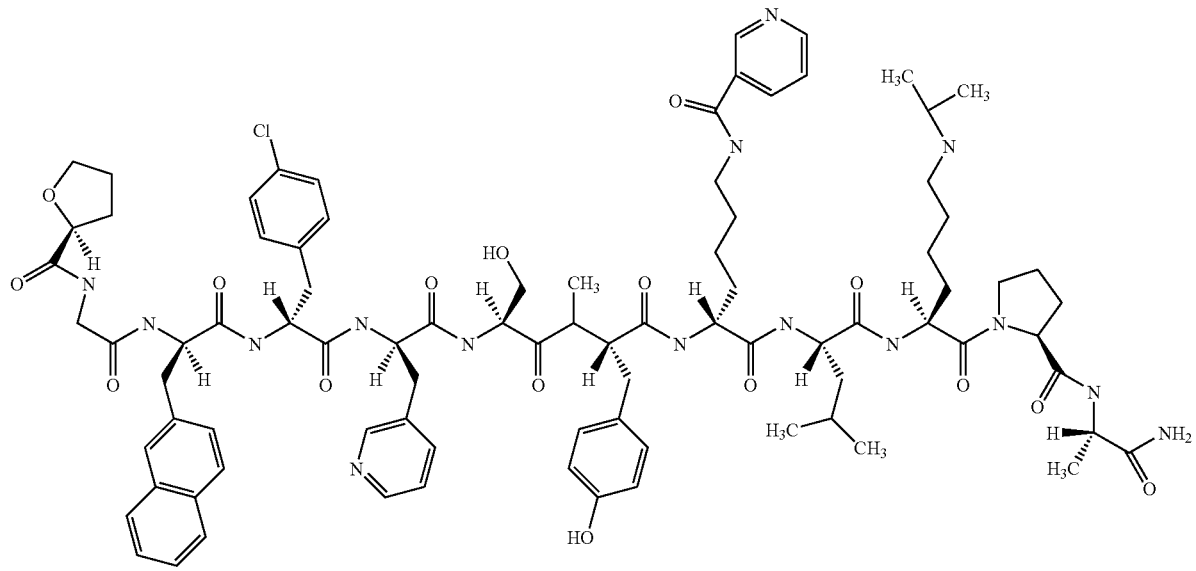

and 685.2 mg of 3-hydroxy-2-naphthoic acid were dissolved in 15 ml of ethanol. This solution was gradually distilled by means of a rotary evaporator to evaporate the organic solvent. This residue was again dissolved in 5.5 ml of dichloromethane and poured in 400 ml of a 0.1% (w/w) aqueous solution of polyvinyl alcohol (EG-40, produced by The Nippon Synthetic Chemical Industry), previously adjusted to 18° C.; the solution was stirred at 8,000 rpm, using a turbine type homomixer, to yield an O/W emulsion. This O/W emulsion was stirred at room temperature for 3 hours to volatilize the dichloromethane and solidify the oil phase, followed by microsphere collection at 2,000 rpm using a centrifuge (05PR-22, Hitachi, Ltd.). The microspheres were again dispersed in distilled water, after which centrifugation was conducted, and the free drug etc. washed down. The microspheres collected were again dispersed in a small amount of distilled water, then freeze-dried, to yield a powder. The recovery rate was 65%, and the peptide A content and 3-hydroxy-2-naphthoic acid/peptide A molar ratio in the microspheres were 75.4% and 1.94, respectively.

Example 2

1,785.1 mg of the acetate of peptide A and 1,370.4 mg of 3-hydroxy-2-naphthoic acid were dissolved in 15 ml of ethanol. This solution was gradually distilled by means of a rotary evaporator to evaporate the organic solvent. This residue was again dissolved in 10 ml of dichloromethane and poured in 1,000 ml of a 0.1% (w/w) aqueous solution of polyvinyl alcohol, previously adjusted to 18° C.; the same procedures as those in Example 1 were followed to yield microspheres. The recovery rate was 58%, the peptide A content and 3-hydroxy-2-naphthoic acid/peptide A molar ratio in the microspheres were 54.3% and 6.15, respectively.

Example 3

1,800 mg of the acetate of peptide A, 173 mg of 3-hydroxy-2-naphthoic acid, and 2 g of a lactic acid-glycolic acid copolymer (lactic acid/glycolic acid=50/50 (mol %), weight-average molecular weight 10,100, number-average molecular weight 5,670, number-average molecular weight 3,720, as determined by terminal group quantitation, produced by Wako Pure Chemical Industries) were dissolved in a mixture of 6 ml of dichloromethane and 0.2 ml of ethanol. This solution was poured into 900 ml of a 0.1% (w/w) aqueous solution of polyvinyl alcohol containing 5% mannitol, previously adjusted to 18° C., and stirred at 7,000 rpm using a turbine type homomixer to yield an O/W emulsion. This O/W emulsion was stirred at room temperature for 3 hours to volatilize the dichloromethane and ethanol and solidify the oil phase, followed by microsphere collection at 2,000 rpm using a centrifuge. The microspheres were again dispersed in distilled water, after which centrifugation was conducted, and the free drug etc. washed down. The microspheres collected were again dispersed in 250 mg of mannitol and a small amount of distilled water, then freeze-dried, to yield a powder. The recovery rate was 76%, the rate of peptide A inclusion in the microspheres was 84.6%, and the peptide A content and 3-hydroxy-2-naphthoic acid/peptide A molar ratio in the microspheres were 34.7% and 1.19, respectively.

Example 4

1,900 mg of the acetate of peptide A, 182 mg of 3-hydroxy-2-naphthoic acid, and 1.9 g of a lactic acid-glycolic acid copolymer (same as in Example 3) were dissolved in a mixture of 6 ml of dichloromethane and 0.2 ml of ethanol. This solution was poured in 900 ml of a 0.1% (w/w) aqueous solution of polyvinyl alcohol containing 5% mannitol and 0.05% L-arginine, previously adjusted to 18° C.; the same procedures as those in Example 3 were followed to yield microspheres. The recovery rate was 85%, the rate of peptide A inclusion in the microspheres was 88.9%, and the peptide A content and 3-hydroxy-2-naphthoic acid/peptide A molar ratio in the microspheres were 38.6% and 0.83, respectively.

Example 5

Microspheres were obtained in the same manner as in Example 4, except that the lactic acid-glycolic acid copolymer used in Example 4 was replaced with a lactic acid-glycolic acid copolymer having a lactic acid/glycolic acid content ratio of 75/25 (mol %), a weight-average molecular weight of 10,700, a number-average molecular weight of 6,100, and a number-average molecular weight of 3,770, as determined by terminal group quantitation, and that the amount of dichloromethane was changed to 6.5 ml. The recovery rate was 87%, the rate of peptide A inclusion in the microspheres was 88.3%, and the peptide A content and 3-hydroxy-2-naphthoic acid/peptide A molar ratio in the microspheres were 38.3% and 0.92, respectively.

Example 6

To a solution of 1,800 mg of the acetate of peptide A and 1.8 g of a lactic acid-glycolic acid copolymer (lactic acid/glycolic acid=50/50 (mol %), weight-average molecular weight 12,700, number-average molecular weight 7,090, number-average molecular weight 4,780, as determined by terminal group quantitation, produced by Wako Pure Chemical Industries) in 7.2 ml of dichloromethane. To this solution, a solution of 196 mg of 3-hydroxy-2-naphthoic acid sodium salt in 2.3 ml of water was added, followed by emulsification using a homogenizer, to yield a W/O emulsion. This emulsion was poured into 800 ml of a 0.1% (w/w) aqueous solution of polyvinyl alcohol containing 5% mannitol, previously adjusted to 18° C., and stirred at 7,000 rpm using a turbine type homomixer to yield a W/O/W emulsion. The same procedures as those in Example 3 were followed to yield microspheres. The recovery rate was 79%, the rate of peptide A inclusion in the microspheres was 81.2%, and the peptide A content and 3-hydroxy-2-naphthoic acid/peptide A molar ratio in the microspheres were 32.8% and 0.91, respectively.

Experimental Example 1

About 40 mg of the microspheres obtained in each of Examples 1 and 2, or about 60 mg of the microspheres obtained in each of Examples 3 through 5, were dispersed in 0.5 ml of a dispersant (distilled water with 0.25 mg of carboxymethyl cellulose, 0.5 mg of Polysorbate 80, and 25 mg of mannitol, all dissolved therein), and subcutaneously administered to the backs of male SD rats at 8 to 10 weeks of age, using a 22G injection needle. After administration, each rat was killed, and the microspheres remaining at the administration site were taken and assayed for peptide A content. The results are shown in Table 1.

TABLE 1

|  | 1 Day | 1 Week | 2 Weeks | 3 Weeks | 4 Weeks |
|---|---|---|---|---|---|
| Example 1 | 73% | 30% | 11% | 6% | 6% |
| Example 2 | 85% | 37% | 9% | 1% |  |
| Example 3 | 70% | 31% | 14% | 9% |  |
| Example 4 | 77% | 29% | 11% | 10% | 6% |
| Example 5 | 81% | 44% | 25% | 17% | 13% |

The experimental results of Examples 1 and 2 demonstrate that the rate of peptide A release from the microspheres consisting of two components, i.e., peptide A and 3-hydroxy-2-naphthoic acid, varied depending on their ratio; peptide A was more rapidly released as the 3-hydroxy-2-naphthoic acid content increased. Also, the experimental results in Examples 3, 4 and 5 demonstrate that the microspheres consisting of three components, i.e., the above two components and a lactic acid-glycolic acid copolymer, showed a peptide A release profile different from that from the microspheres consisting of the two. It was also shown that the release behavior of microspheres can be controlled by combining different lactic acid-glycolic acid copolymer compositions and weight-average molecular weights. The results in Example 7 and Reference Example 1 demonstrate that 3-hydroxy-2-naphthoic acid increases the peptide B content in microspheres.

Example 7

A solution of 0.8 g of the acetate of 5-oxo-Pro-His-Trp-Ser-Tyr-DLeu-Leu-Arg-Pro-NH—$C_2H_5$ (SEQ ID NO.: 5) (hereinafter referred to as peptide B, produced by Takeda Chemical) in 0.8 ml of distilled water was mixed with a solution of 3.08 g of a DL-lactic acid polymer (weight-average molecular weight 36,000, number-average molecular weight 18,000, carboxyl group content based on labeling quantitation method 70.4 µmol/g) and 0.12 g of 3-hydroxy-2-naphthoic acid in a mixed organic solvent of 5 ml of dichloromethane and 0.3 ml of ethanol, and this mixture was emulsified in a homogenizer to yield a W/O emulsion. This W/O emulsion was injected to 800 ml of a 0.1% (w/w) aqueous solution of polyvinyl alcohol (EG-40, produced by The Nippon Synthetic Chemical Industry), previously adjusted to 15° C., and stirred at 7,000 rpm using a turbine type homomixer to yield a W/O/W emulsion. This W/O/W emulsion was stirred at room temperature for 3 hours to volatilize or diffuse in the external aqueous phase the dichloromethane and ethanol, to solidify the oil phase, after which the oil phase was sieved through a sieve of 75 µm pore size, followed by centrifugation at 2,000 rpm for 5 minutes in a centrifuge (05PR-22, Hitachi, Ltd.) to sediment microcapsules, which were collected. The microcapsules were again dispersed in distilled water, then centrifuged, followed by washing free drug etc. and microcapsule collection. The microcapsules were re-dispersed in a small amount of distilled water added, after which they were freeze-dried to yield a powder. The microcapsule mass recovery rate was 46%, the microcapsule peptide B content and 3-hydroxy-2-naphthoic acid content being 21.3% and 2.96%, respectively. The inclusion efficiencies as determined by dividing these actual contents by the respective charge contents were 106.6% for peptide B and 98.6% for 3-hydroxy-2-naphthoic acid.

Example 8

A solution of 1.2 g of the acetate of peptide B in 1.2 ml of distilled water was mixed with a solution of 4.62 g of a DL-lactic acid polymer (weight-average molecular weight 25,200, number-average molecular weight 12,800, carboxyl group content based on labeling quantitation method 62.5 µmol/g) and 0.18 g of 3-hydroxy-2-naphthoic acid in a mixed organic solvent of 7.5 ml of di-chloromethane and 0.45 ml of ethanol, and this mixture was emulsified in a homogenizer to yield a W/O emulsion. This W/O emulsion was then injected to 1,200 ml of a 0.1% (w/w) aqueous solution of polyvinyl alcohol (EG-40, produced by The Nippon Synthetic Chemical Industry), previously adjusted to 15° C., and stirred at 7,000 rpm using a turbine type homomixer to yield a W/O/W emulsion. This W/O/W emulsion was stirred at room temperature for 3 hours to volatilize or diffuse in the external aqueous phase the dichloromethane and ethanol, to solidify the oil phase, after which the oil phase was sieved through a sieve of 75 µm pore size, followed by centrifugation at 2,000 rpm for 5 minutes in a centrifuge (05PR-22, Hitachi, Ltd.) to sediment microcapsules, which were collected. The micro-capsules were again dispersed in distilled water, then centrifuged, followed by washing free drug etc. and micro-capsule collection. The microcapsules were re-dispersed in a small amount of distilled water, and 0.3 g of mannitol was added and dissolved, after which the solution was freeze-dried to yield a powder. The microcapsule mass recovery rate as determined by subtracting the amount of mannitol added was 55.2%, the microcapsule peptide B content and 3-hydroxy-2-naphthoic acid content being 21.3% and 2.96%, respectively. The inclusion efficiencies as determined by dividing these actual contents by the respective charge contents were 99.7% for peptide B and 102.2% for 3-hydroxy-2-naphthoic acid.

Example 9

A microcapsule powder was obtained in the same manner as in Example 8, except that the DL-lactic acid polymer described in Example 8 was replaced with another DL-lactic acid polymer (weight-average molecular weight 28,800, number-average molecular weight 14,500, carboxyl group content based on labeling quantitation method 78.1 µmol/g). The microcapsule mass recovery rate as determined by subtracting the amount of mannitol added was 50.2%, the microcapsule peptide B content and 3-hydroxy-2-naphthoic acid content being 20.8% and 2.78%, respectively. The inclusion efficiencies as determined by dividing these actual contents by the respective charge contents were 103.4% for peptide B and 92.7% for 3-hydroxy-2-naphthoic acid.

Comparative Example 1

A solution of 1.2 g of the acetate of peptide B in 1.2 ml of distilled water was mixed with a solution of 4.8 g of the same DL-lactic acid polymer as of Example 9 in 7.8 ml of dichloromethane, and this mixture was injected to 1,200 ml of a 0.1% (w/w) aqueous solution of polyvinyl alcohol (EG-40, produced by The Nippon Synthetic Chemical Industry), previously adjusted to 15° C., and stirred at 7,000 rpm using a turbine type homomixer to yield a W/O/W emulsion. This W/O/W emulsion was treated in the same manner as in Example 8 to yield a microcapsule powder. The microcapsule mass recovery rate as determined by subtracting the amount of mannitol added was 53.6%, the microcapsule peptide B content being 12.1%. The peptide B inclusion efficiency as determined by dividing the actual content by the charge content was 60.6%, a rate much lower than that obtained in Example 9. It is therefore evident that peptide B inclusion efficiency was increased by the addition of 3-hydroxy-2-naphthoic acid.

Example 10

A solution of 1.00 g of the acetate of peptide B in 1.00 ml of distilled water was mixed with a solution of 3.85 g of a DL-lactic acid polymer (weight-average molecular weight 49,500, number-average molecular weight 17,500, carboxyl group content based on labeling quantitation method 45.9 µmol/g) and 0.15 g of 3-hydroxy-2-naphthoic acid in a mixed organic solvent of 7.5 ml of di-chloromethane and 0.4 ml of ethanol, and this mixture was emulsified in a homogenizer to yield a W/O emulsion. This W/O emulsion was then treated in the same manner as in Example 8, except that the amount of 0.1% (w/w) aqueous solution of polyvinyl alcohol and the amount of mannitol added were changed to 1,000 ml and 0.257 g, respectively, to yield a microcapsule powder. The microcapsule mass recovery rate as determined by subtracting the amount of mannitol added was 53.8%, the microcapsule peptide B content and 3-hydroxy-2-naphthoic acid content being 18.02% and 2.70%, respectively. The inclusion efficiencies as determined by dividing these actual contents by the respective charge contents were 90.1% for peptide B and 90.1% for 3-hydroxy-2-naphthoic acid.

Example 11

A solution of 1.202 g of the acetate of peptide B in 1.20 ml of distilled water was mixed with a solution of 4.619 g of a DL-lactic acid polymer (weight-average molecular weight 19,900, number-average molecular weight 10,700, carboxyl group content based on labeling quantitation method 104.6 µmol/g) and 0.179 g of 3-hydroxy-2-naphthoic acid in a mixed organic solvent of 7.5 ml of dichloromethane and 0.45 ml of ethanol, and this mixture was emulsified in a homogenizer to yield a W/O emulsion. This W/O emulsion was then treated in the same manner as in Example 8, except that the amount of mannitol added was 0.303 g, to yield a microcapsule powder. The microcapsule mass recovery rate as determined by subtracting the amount of mannitol added was 61.4%, the microcapsule peptide B content and 3-hydroxy-2-naphthoic acid content being 15.88% and 2.23%, respectively. The inclusion efficiencies as determined by dividing these actual contents by the respective charge contents were 77.75% for peptide B and 75.05% for 3-hydroxy-2-naphthoic acid.

Example 12

A solution of 1.00 g of the acetate of peptide B in 1.00 ml of distilled water was mixed with a solution of 3.85 g of a DL-lactic acid polymer (weight-average molecular weight 25,900, number-average molecular weight 7,100, carboxyl group content based on labeling quantitation method 98.2 µmol/g) and 0.15 g of 3-hydroxy-2-naphthoic acid in a mixed organic solvent of 5.5 ml of di-chloromethane and 0.35 ml of ethanol, and this mixture was emulsified in a homogenizer to yield a W/O emulsion. This W/O emulsion was then treated in the same manner as in Example 7 to yield a microcapsule powder. The microcapsule mass recovery rate was 48.8%, the microcapsule peptide B content and 3-hydroxy-2-naphthoic acid content being 21.31% and 2.96%, respectively. The inclusion efficiencies as determined by dividing these actual contents by the respective charge contents were 106.5% for peptide B and 98.7% for 3-hydroxy-2-naphthoic acid.

Comparative Example 2

A solution of 1.00 g of the acetate of peptide B in 1.00 ml of distilled water was mixed with a solution of 4.00 g of the same DL-lactic acid polymer as of Example 12 in 5 ml of dichloromethane, and this mixture was emulsified in a homogenizer to yield a W/O emulsion. This W/O emulsion was then treated in the same manner as in Example 7 to yield a microcapsule powder. The microcapsule mass recovery rate was 48.7%, the microcapsule peptide B content being 11.41%. The inclusion efficiency as determined by dividing this actual content by the charge content was 57.1%, a rate much lower than that obtained in Example 12. It is therefore evident that peptide B inclusion efficiency was increased by the addition of 3-hydroxy-2-naphthoic acid.

Example 13

A solution of 89.2 g of a DL-lactic acid polymer (weight-average molecular weight 30,600, number-average molecular weight 14,400, carboxyl group content based on labeling quantitation method 63.0 µmol/g) in 115.3 g of dichloromethane was mixed with a solution of 3.45 g of 3-hydroxy-2-naphthoic acid in a mixed organic solvent of 38.8 g of dichloromethane and 6.27 g of ethanol, and this mixture was adjusted to 28.5° C. From this organic solvent solution, 224 g was weighed out and mixed with an aqueous solution of 22.3 g of the acetate of peptide B in 20 ml of distilled water, previously warmed to 44.9° C., followed by 5 minutes of stirring, to yield a crude emulsion, which was then emulsified at 10,000 rpm for 5 minutes in a homogenizer to yield a W/O emulsion. This W/O emulsion was then cooled to 16.3° C., and injected to 20 liters of a 0.1% (w/w) aqueous solution of polyvinyl alcohol (EG-40, produced by The Nippon Synthetic Chemical Industry), previously adjusted to 15° C., over a 5-minute period, and stirred at 7,000 rpm using HOMOMIC LINE FLOW (produced by Tokushu Kika) to yield a W/O/W emulsion. This W/O/W emulsion was stirred at 15° C. for 3 hours to volatilize or diffuse in the external aqueous phase the dichloromethane and ethanol, to solidify the oil phase, after which the oil phase was sieved through a sieve of 75 µm pore size, followed by centrifugation at 2,000 rpm in a centrifuge (H-600S, produced by Kokusan Enshinki) to continuously sediment microcapsules, which were collected. The microcapsules were again dispersed in a small amount of distilled water, then sieved through a sieve of 90 µm pore size, followed by freeze drying, to yield a powder. The microcapsule mass recovery rate as determined by subtracting the amount of mannitol added was 66.5%, the microcapsule peptide B content and 3-hydroxy-2-naphthoic acid content being 22.3% and 2.99%, respectively. The inclusion efficiencies as determined by dividing these actual contents by the respective charge contents were 104.5% for peptide B and 102.1% for 3-hydroxy-2-naphthoic acid.

Experimental Example 2

A dispersion of about 45 mg of microcapsules as described in Example 8 in 0.3 ml of a dispersant (distilled water containing 0.15 mg of carboxymethyl cellulose, 0.3 mg of polysorbate 80, and 15 mg of mannitol all dissolved therein) was subcutaneously administered to the backs of male SD rats at 7 weeks of age, using a 22G injection needle. After given time intervals, rats were killed, and microcapsules remaining at the injection site were taken and quantitatively assayed for peptide B and 3-hydroxy-2-naphthoic acid. The retention rates as determined by dividing the assay values by the respective initial contents, and the property profiles of the DL-lactic acid polymer used are shown in Table 2.

TABLE 2

Characteristics of the Microcapsule DL-Lactic Acid Polymer Described in Example 8

| Mw (Da) | 25,200 |
|---|---|
| [COOH] (μmol/g polymer) | 62.5 |

Retention rate:

| | Peptide B | 3-Hydroxy-2-naphthoic acid |
|---|---|---|
| 1 day | 93.1% | 91.0% |
| 2 weeks | 84.2% | 54.1% |
| 4 weeks | 75.7% | 34.5% |
| 8 weeks | 63.0% | 5.1% |
| 12 weeks | 46.9% | 0.0% |
| 16 weeks | 31.7% | 0.0% |
| 20 weeks | 24.0% | 0.0% |

As seen in Table 2, the microcapsule described in Example 8 shows a dramatically high bioactive substance retention rate of not less than 90% at 1 day after administration, despite the high bioactive substance content. It is therefore evident that 3-hydroxy-2-naphthoic acid is effective not only in allowing bioactive substance incorporation at high contents in sustained-release preparations, but also in very well suppressing initial burst of bioactive substances. This microcapsule is capable of releasing a bioactive substance at a constant rate over a very long period of time. In addition, although 3-hydroxy-2-naphthoic acid has completely been eliminated from the microcapsule after 12 weeks, the same bioactive substance release rate is maintained, demonstrating efficacy as a sustained-release preparation.

Experimental Example 3

After microcapsules as obtained in Examples 7 and 9-12 and Comparative Example 1 were administered and recovered in the same manner as in Experimental Example 2, peptide B therein was quantified. The retention rates as determined by dividing the assay values by the respective initial contents, and the property profiles of the DL-lactic acid polymer used are shown in Table 3.

TABLE 3

Characteristics of the DL-Lactic Acid Polymers:

| | Example 7 | Example 9 | Example 10 | Example 11 | Example 12 | Comparative Example 1 |
|---|---|---|---|---|---|---|
| Mw (Da) | 36,000 | 28,800 | 49,500 | 19,900 | 25,900 | 28,800 |
| [COOH] (μmol/g polymer) | 70.4 | 78.1 | 45.9 | 104.6 | 98.2 | 78.1 |
| Retention rate | | | | | | |
| 1 day | 92.9% | 94.6% | 93.0% | 92.3% | 89.4% | 83.1% |
| 2 weeks | 82.2% | 82.2% | 80.4% | 37.5% | 34.3% | 73.0% |
| 4 weeks | 69.6% | 69.2% | 58.3% | 30.7% | 29.7% | 65.3% |
| 8 weeks | 62.1% | 56.0% | 36.6% | 24.6% | 20.8% | |
| 12 weeks | 47.9% | 39.4% | 30.8% | 18.6% | | |
| 16 weeks | 32.2% | | 28.0% | | | |
| 20 weeks | (not determined) | | 22.9% | | | |
| 24 weeks | 11.6% | | | | | |
| 28 weeks | 4.1% | | | | | |

As seen in Tables 2 and 3, the microcapsules described in Examples 7 through 12 show dramatically higher retention rates of about 90% or higher at 1 day after administration, as compared with Comparative Example 1. It is therefore evident that 3-hydroxy-2-naphthoic acid is effective not only in allowing bioactive substance incorporation at high contents in sustained-release preparations, but also in very well suppressing initial burst of bioactive substances. Experiments using the microcapsules described in Examples 7 through 9, in particular, demonstrate that when DL-lactic acids with weight-average molecular weights of about 20,000 to about 50,000, and carboxyl group contents of about 50 to 90 μmol/g, as determined by the labeling quantitation method, are used, it is possible to release a bioactive substance at a constant rate over a very long period of time.

Experimental Example 4

After the microcapsule obtained in Example 7 was subcutaneously administered to rats by the method described in Experimental Example 2, blood was collected, and serum peptide B and testosterone concentrations were determined. The results are shown in Table 4.

TABLE 4

| | 12 weeks | 16 weeks | 24 weeks | 26 weeks | 28 weeks |
|---|---|---|---|---|---|
| Peptide B (ng/ml) | 1.10 | 1.65 | 1.46 | 2.73 | 1.30 |
| Testosterone (ng/ml) | 0.18 | 0.45 | 0.68 | 0.41 | 0.71 |

As seen in Table 4, the blood bioactive substance concentration was kept at constant levels until 28 weeks after administration, meaning that the bioactive substance was continuously released from the microcapsule over a 28-week period. It was shown that the pharmacologically active testosterone concentration was constantly suppressed below normal levels during that period, and that the bioactive substance was stably present in, and released from, the microcapsule over a long period of time, without losing its activity, even when 3-hydroxy-2-naphthoic acid was contained in the preparation.

Example 14

A 0.5 N aqueous solution of sodium hydroxide/methanol mixture (v/v=1/5) was passed through a strongly basic ion exchange column (SeP-Pak Plus QMA Cartridge, produced by WATERS) to eliminate chloride ions. After the effluent became non-responsive to the addition of a silver nitrate solution acidified with nitric acid to show white turbidity, a water/methanol mixture (v/v=1/5) was passed to eliminate the excess alkali. After confirmation of effluent neutrality, 18.8 mg of the acetate of peptide B was dissolved in 2 ml of a water/methanol mixture (v/v=1/5) and passed through a column pretreated as described above. This effluent and another effluent resulting from passage of 6 ml of the mixture alone were combined; this mixture was mixed with a solution of 5.91 mg of 3-hydroxy-2-naphthoic acid in 1 ml of a water/methanol mixture (v/v=1/5), followed by concentration using a rotary evaporator. Upon white turbidity formation in the mixture, 2 ml of water was added, followed by stirring. After centrifugation (3,000 rpm, 20° C., 15 minutes), the supernatant was removed, followed by several cycles of water washing, after which the precipitate was vacuum dried (40° C., overnight) to yield 4.09 mg of the 3-hydroxy-2-naphthoic acid salt of peptide B.

To this salt, 0.5 ml of water was added, followed by stirring at room temperature for 4 hours, after which the liquid was filtered through a 0.2 μm filter and quantified by HPLC. The peptide B and 3-hydroxy-2-naphthoic acid concentrations were 2.37 g/l and 0.751 g/l, respectively. The salt partially remained non-dissolved even after stirring; the above values are assumed to represent the water solubility of the 3-hydroxy-2-naphthoic acid salt of peptide B, not more than 1/100 lower than the water solubility, not less than 1,000 g/l, of the acetate of peptide B. This demonstrates that the 3-hydroxy-2-naphthoic acid salt of peptide B can be used as a peptide B sustained-release preparation.

EFFECT OF THE INVENTION

The sustained-release composition of the present invention contains a biologically active substance at high concentration, and is capable of a controlled rate of release.

The invention claimed is:

1. A method of producing a sustained-release composition containing an LH-RH derivative or salt thereof, a hydroxynaphthoic acid or salt thereof and a biodegradable polymer or salt thereof, comprising removing an organic solvent from a mixture comprising the organic solvent, an LH-RH derivative or salt thereof, a biodegradable polymer or salt thereof, and hydroxynaphthoic acid or a salt thereof.

2. The method of claim 1, comprising mixing and dispersing an LH-RH derivative or salt thereof in an organic solvent solution containing a biodegradable polymer or salt thereof and hydroxynaphthoic acid or a salt thereof, and subsequently removing the organic solvent.

3. The method of claim 2, wherein the LH-RH derivative or salt thereof is in the form of an aqueous solution.

4. The method of claim 1, wherein the salt of the LH-RH derivative is a salt with a free base or acid.

5. A method of suppressing initial burst of an LH-RH derivative from a sustained-release composition by maintaining a retention rate, comprising adding hydroxynaphthoic acid or a salt thereof to the sustained-release composition.

6. A method of prolonging the efficiency of an LH-RH derivative in a sustained-release composition, comprising adding hydroxynaphthoic acid or a salt thereof to the sustained-release composition.

7. A hydroxynaphthoate of an LH-RH derivative.

8. The hydroxynaphthoate of an LH-RH derivative claim 7, which is soluble in water or very slightly soluble in water.

9. A sustained-release composition containing the hydroxynaphthoate of an LH-RH derivative.

* * * * *

SEQUENCE LISTING

```
<160> NUMBER OF SEQ ID NOS: 5

<210> SEQ ID NO 1
<211> LENGTH: 10
<212> TYPE: PRT
<213> ORGANISM: artificial sequence
<220> FEATURE:
<223> OTHER INFORMATION: LH-RH peptide derivative/analog
<220> FEATURE:
<221> NAME/KEY: MISC_FEATURE
<222> LOCATION: (1)..(1)
<223> OTHER INFORMATION: 5-oxo-Pro
<220> FEATURE:
<221> NAME/KEY: MISC_FEATURE
<222> LOCATION: (6)..(6)
<223> OTHER INFORMATION: DLeu, DAla, DTrp, DSer(tbut), D2Nal or
     DHis(ImBzl)
<220> FEATURE:
<221> NAME/KEY: MISC_FEATURE
<222> LOCATION: (9)..(9)
<223> OTHER INFORMATION: Pro or Pro-NH-C2H5
<220> FEATURE:
<221> NAME/KEY: MISC_FEATURE
<222> LOCATION: (10)..(10)
<223> OTHER INFORMATION: Gly-NH2 or nothing

<400> SEQUENCE: 1

Pro His Trp Ser Tyr Xaa Leu Arg Pro Xaa
1               5                   10

<210> SEQ ID NO 2
<211> LENGTH: 11
<212> TYPE: PRT
<213> ORGANISM: Artificial Sequence
<220> FEATURE:
<223> OTHER INFORMATION: LH-RH antagonist derivative/analog
<220> FEATURE:
<221> NAME/KEY: MISC_FEATURE
<222> LOCATION: (1)..(1)
<223> OTHER INFORMATION: N(4H2-furoyl)Gly or Nac
<220> FEATURE:
<221> NAME/KEY: MISC_FEATURE
<222> LOCATION: (2)..(2)
<223> OTHER INFORMATION: D2Nal
<220> FEATURE:
<221> NAME/KEY: MISC_FEATURE
<222> LOCATION: (3)..(3)
```

```
<223> OTHER INFORMATION: D4ClPhe
<220> FEATURE:
<221> NAME/KEY: MISC_FEATURE
<222> LOCATION: (4)..(4)
<223> OTHER INFORMATION: D3Pal
<220> FEATURE:
<221> NAME/KEY: MISC_FEATURE
<222> LOCATION: (6)..(6)
<223> OTHER INFORMATION: NMeTyr, Tyr, Aph(Atz) and NMeAph(Atz)
<220> FEATURE:
<221> NAME/KEY: MISC_FEATURE
<222> LOCATION: (7)..(7)
<223> OTHER INFORMATION: DLys(Nic), DCit, DLys(AzaglyNic),
      DLys(AzaglyFur), DhArg(Et2), DAph(Atz), DhCi.
<220> FEATURE:
<221> NAME/KEY: MISC_FEATURE
<222> LOCATION: (9)..(9)
<223> OTHER INFORMATION: Lys(Nisp), Arg, hArg(Et2).
<220> FEATURE:
<221> NAME/KEY: MISC_FEATURE
<222> LOCATION: (11)..(11)
<223> OTHER INFORMATION: DAlaNH2

<400> SEQUENCE: 2

Xaa Xaa Xaa Xaa Ser Xaa Xaa Leu Xaa Pro Xaa
1               5                   10

<210> SEQ ID NO 3
<211> LENGTH: 8
<212> TYPE: PRT
<213> ORGANISM: Artificial Sequence
<220> FEATURE:
<223> OTHER INFORMATION: LH-RH peptide derivative/analog
<220> FEATURE:
<221> NAME/KEY: MISC_FEATURE
<222> LOCATION: (1)..(1)
<223> OTHER INFORMATION: 5-oxo-Pro
<220> FEATURE:
<221> NAME/KEY: MISC_FEATURE
<222> LOCATION: (6)..(6)
<223> OTHER INFORMATION: Dleu
<220> FEATURE:
<221> NAME/KEY: MISC_FEATURE
<222> LOCATION: (8)..(8)
<223> OTHER INFORMATION: Pro-NH-C2H5

<400> SEQUENCE: 3

Pro His Trp Ser Tyr Xaa Arg Pro
1               5

<210> SEQ ID NO 4
<211> LENGTH: 11
<212> TYPE: PRT
<213> ORGANISM: Artificial Sequence
<220> FEATURE:
<223> OTHER INFORMATION: LH-RH peptide derivative/analog
<220> FEATURE:
<221> NAME/KEY: MISC_FEATURE
<222> LOCATION: (1)..(1)
<223> OTHER INFORMATION: N-(S)-tetrahydrofur-2-oyl-Gly
<220> FEATURE:
<221> NAME/KEY: MISC_FEATURE
<222> LOCATION: (2)..(2)
<223> OTHER INFORMATION: D2Nal
<220> FEATURE:
<221> NAME/KEY: MISC_FEATURE
<222> LOCATION: (3)..(3)
<223> OTHER INFORMATION: D4ClPhe
<220> FEATURE:
<221> NAME/KEY: MISC_FEATURE
<222> LOCATION: (4)..(4)
<223> OTHER INFORMATION: D3Pal
<220> FEATURE:
<221> NAME/KEY: MISC_FEATURE
<222> LOCATION: (6)..(6)
```

```
<223> OTHER INFORMATION: NmeTyr
<220> FEATURE:
<221> NAME/KEY: MISC_FEATURE
<222> LOCATION: (7)..(7)
<223> OTHER INFORMATION: DLys(Nic)
<220> FEATURE:
<221> NAME/KEY: MISC_FEATURE
<222> LOCATION: (9)..(9)
<223> OTHER INFORMATION: Lys(Nisp)
<220> FEATURE:
<221> NAME/KEY: MISC_FEATURE
<222> LOCATION: (11)..(11)
<223> OTHER INFORMATION: DAlaNH2

<400> SEQUENCE: 4

Gly Xaa Xaa Xaa Ser Xaa Xaa Leu Xaa Pro Xaa
1               5                   10

<210> SEQ ID NO 5
<211> LENGTH: 9
<212> TYPE: PRT
<213> ORGANISM: Artificial Sequence
<220> FEATURE:
<223> OTHER INFORMATION: LH-RH peptide derivative/analog
<220> FEATURE:
<221> NAME/KEY: MISC_FEATURE
<222> LOCATION: (1)..(1)
<223> OTHER INFORMATION: 5-oxo-Pro
<220> FEATURE:
<221> NAME/KEY: MISC_FEATURE
<222> LOCATION: (6)..(6)
<223> OTHER INFORMATION: Dleu
<220> FEATURE:
<221> NAME/KEY: MISC_FEATURE
<222> LOCATION: (9)..(9)
<223> OTHER INFORMATION: Pro-NH-C2H5

<400> SEQUENCE: 5

Pro His Trp Ser Tyr Xaa Leu Arg Pro
1               5
```